(12) United States Patent
Shen et al.

(10) Patent No.: US 12,234,241 B2
(45) Date of Patent: Feb. 25, 2025

(54) IMIDAZOTRIAZINE THIOBENZAMIDE DERIVATIVE, AND PREPARATION METHOD AND APPLICATION THEREOF

(71) Applicant: Yunbaiyao Zhengwu Science and Technology (Shanghai) Co., Ltd., Shanghai (CN)

(72) Inventors: Zhengwu Shen, Shanghai (CN); Bin Deng, Kunming (CN); Yunxiang Fan, Kunming (CN); Yangli Shen, Kunming (CN); Xuejiang Chen, Kunming (CN); Yinshuang Wu, Kunming (CN); Xinyi Wang, Shanghai (CN); Hongzhu Bian, Shanghai (CN)

(73) Assignee: Yunbaiyao Zhengwu Science and Technology (Shanghai) Co., Ltd., Shanghai (CN)

( * ) Notice: Subject to any disclaimer, the term of this patent is extended or adjusted under 35 U.S.C. 154(b) by 0 days.

(21) Appl. No.: 18/634,599

(22) Filed: Apr. 12, 2024

(65) Prior Publication Data
US 2024/0294535 A1    Sep. 5, 2024

(30) Foreign Application Priority Data

May 16, 2023   (CN) .......................... 202310553789.2

(51) Int. Cl.
*C07D 487/04*  (2006.01)
*A61K 31/53*   (2006.01)
*A61P 35/00*   (2006.01)

(52) U.S. Cl.
CPC ............ *C07D 487/04* (2013.01); *A61K 31/53* (2013.01); *A61P 35/00* (2018.01)

(58) Field of Classification Search
CPC ........ C07D 487/04; A61P 35/00; A61K 31/53
See application file for complete search history.

(56) References Cited

FOREIGN PATENT DOCUMENTS

| CN | 101641093 A | 2/2010 | |
|---|---|---|---|
| CN | 105168241 A | 12/2015 | |
| WO | WO-2008064157 A1 * | 5/2008 | ........... A61K 31/198 |

OTHER PUBLICATIONS

Bianchi et al. (Current Opinion in Cell Biology. 2020; 63:135-143) (Year: 2020).*
Schafer et al. Drug Discovery Today 2008, 13 (21/22), 913-916 (Year: 2008).*
Horig et al. Journal of Translational Medicine 2004, 2(44) (Year: 2004).*
Kumari et al. (J Med Chem. Nov. 12, 2020; 63(21): 12290-12358) (Year: 2020).*
Zheng Wei Lee et al., "The slow-releasing hydrogen sulfide donor, GYY4137, exhibits novel anti-cancer effects in vitro and in vivo", PLoS one, Jun. 2011, vol. 6, Issue 6, e21077, Entire document.
Khosrow Kashfi, "Anti-cancer activity of new designer hydrogen sulfide-donating hybrids", Antioxidants & Redox Signaling, Feb. 10, 2014, vol. 20, No. 5, pp. 831-846.
Csaba Szabo, "Gasotransmitters in cancer: from pathophysiology to experimental therapy", Nature Reviews Drug Discovery, Mar. 2016, vol. 15, No. 3, Entire document.
Xu Cao et al., "A Review of Hydrogen Sulfide Synthesis, Metabolism, and Measurement: Is Modulation of Hydrogen Sulfide a Novel Therapeutic for Cancer?", Antioxidants & Redox Signaling, 2019, vol. 31, No. 1, pp. 1-38.
Fangfang Cai et al., "ADT-OH, a hydrogen sulfide-releasing donor, induces apoptosis and inhibits the development of melanoma in vivo by upregulating FADD", Cell Death and Disease, Jan. 16, 2020, 11(1):33, Entire document.
Z-W Lee et al., "Utilizing hydrogen sulfide as a novel anti-cancer agent by targeting cancer glycolysis and pH imbalance." British Journal of Pharmacology, 2014, vol. 171, No. 18, pp. 4322-4336.
Yang Liu et al., "Recent progress in bioactive gas delivery for cancer immunotherapy", Progress in Biomedical Engineering, 2022, 4(2), Entire document.
Donald Rosenthal et al., "A Study of the Mechanism and Kinetics of the Thioacetamide Hydrolysis Reaction", Journal of the American Chemical Society, 1957, vol. 79, No. 11, pp. 2684-2690.

* cited by examiner

*Primary Examiner* — Daniel R Carcanague
*Assistant Examiner* — Jerica Katlynn Wilson

(57) ABSTRACT

Provided is an imidazotriazine thiobenzamide derivative of formula (I),

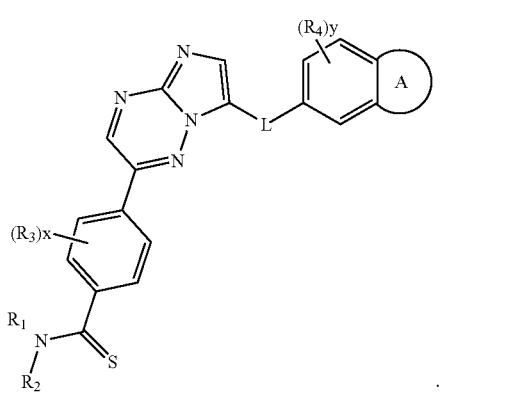

A preparation method for the imidazotriazine thiobenzamide derivative, and a use of the imidazotriazine thiobenzamide derivative or an isomer, a pharmaceutically-acceptable salt, or a prodrug thereof in the preparation of drugs for the treatment of cancer are also provided.

9 Claims, 2 Drawing Sheets

IMIDAZOTRIAZINE THIOBENZAMIDE DERIVATIVE, AND PREPARATION METHOD AND APPLICATION THEREOF

CROSS-REFERENCE TO RELATED APPLICATIONS

This application claims the benefit of priority from Chinese Patent Applications No. 202310553789.2, filed on May 16, 2023, and No. 202310541621.X, filed on May 15, 2023. The content of the aforementioned application, including any intervening amendments thereto, is incorporated herein by reference in its entirety.

TECHNICAL FIELD

This application relates to pharmaceutical chemistry, and more particularly to an imidazotriazine thiobenzamide derivative for cancer treatment, and a preparation method and application thereof.

BACKGROUND

There are few examples of compounds with thioamide structures for cancer treatment. Since the sulfur atom has one electron shell more than the oxygen atom, the gravitational force of the sulfur nucleus on the outermost electron shell is weak, and the outermost electron can easily delocalize to undergo polarization deformation. This results in the bond length of the thiocarbonyl (C=S) being longer than that of the carbonyl bond (C=O), and the bond length of the carbon-nitrogen (C—N) bond in the thioamide being shorter than that of the amide. Compared to the amide, the thioamide is a weaker hydrogen-bond acceptor. Therefore, the use of the thioamide as a bioisostere of amide may reduce the strength of the hydrogen bond. In addition, the size of the sulfur atom is much larger than that of the oxygen atom, so molecules with the thioamide moiety may more easily be off-target compared to amide. However, the sulfur atom has a better electron-donating characteristic than oxygen, and it can easily coordinate with metal ions and reduce the C=S bond energy. The reaction will take place on the C=S bond when attacked by the electron-deficient group. The reaction is normally difficult to occur on the C=O bond under the same conditions. For example, the sulfur atom is easily oxidized, so the thioamide is less stable than the corresponding amide. Therefore, there are few reports of the substitution of amides with thioamides in medicinal chemistry studies.

In 2005, scientists discovered hydrogen sulfide, the third endogenous gaseous transmitter after nitric oxide and carbon monoxide, which is very important for human health. It rapidly crosses cell membranes and exerts important physiological effects such as vasodilatation, cardioprotection, anti-inflammatory, antioxidant and antitumor effects. (PLOS One, 2011, 6(6): e21077; Antioxid Redox Signal, 2014, 20 (5):831-846; Nat Rev Drug Discov, 2016, 15(3): 185-203; Antioxid Redox Signal, 2019, 31(1): 1-38). Compounds containing hydrogen sulfide donor moiety release hydrogen sulfide upon hydrolysis, which inhibits the activation of nuclear factor NF-κB, reduces the expression of NF-κB and thus induces apoptosis of melanoma B6F10. It also up-regulates the expressions of the corresponding Fas-Associated protein with Death Domain (FADD), thereby inhibiting the growth of melanoma in vivo (Cell Death Dis. 2020, 11(1), 33). Hydrogen sulfide has been reported to promote glucose uptake by cancer cells, accelerate the rate of glycolysis and lactic acid production, disrupt intercellular acid efflux, and lower the pH in cancer cells, thereby inhibiting cancer cell proliferation. Hydrogen sulfide may also disrupt mitochondria function, activate apoptotic pathways, and block the G1/S phase of the cell cycle, thereby exerting antitumor effects (Br. J. Pharmacol., 2014,171(18), 4322-36). Researchers have developed a novel antitumor immunotherapy strategy to deliver hydrogen sulfide into the tumor microenvironment (Progress in Biomedical Engineering, 2022, 4(2), art. no. 022001). It has also been reported that endogenous hydrogen sulfide synergistically enhances the antitumor activity of chemotherapeutic drugs (CN105168241B).

Hydrolysis of thioamide under acidic or alkaline conditions has been reported to release hydrogen sulfide (Journal of the American Chemical Society, 1957, 79: 2684-2690). Thus, the thioamide derivatives described in the present disclosure can release hydrogen sulfide by hydrolysis in the presence of enzymes, and are likely to have synergistic antitumor activity with chemotherapeutic agents.

The c-Met signal pathway is abnormally expressed or mutated in various solid tumors, such as lung, gastric, liver and breast cancers, and plays a crucial role in tumorigenesis and tumor development. As a therapeutic target for these tumors, c-Met inhibitors hold promise in the search for novel antitumor drugs due to their clear mechanism of action, easy of synthesis and easy of modification. Small molecule c-Met inhibitors bind to the c-Met receptor, inhibiting the phosphorylation of c-Met binding domain, preventing the activation of tyrosine kinase, and suppressing tumor signal transduction. Compared to traditional antitumor drugs, c-Met inhibitors exhibit fewer side effects and better therapeutic efficacy, and have therefore been continuously introduced into the clinical practice as antitumor drugs.

Capmatinib, as the c-MET inhibitor, was approved by the US Food and Drug Administration (FDA) on May 6, 2020, for the treatment of patients with metastatic non-small cell lung cancer (NSCLC) that is not surgically resectable and harbors a mesenchymal-epithelial transformation (c-MET) exon 14 mutation. However, Capmatinib is associated with significant toxicity and can cause various side effects that should not be overlooked, including interstitial lung disease/pneumonia, hepatotoxicity, peripheral edema and nephrotoxicity. It is important to carefully monitor patients receiving Capmatinib treatment and manage any potential adverse reactions promptly.

A structure of Capmatinib is shown as follows:

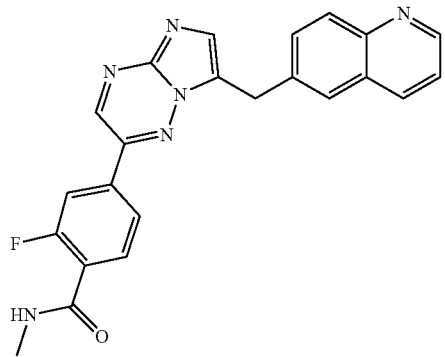

Structural modifications to Capmatinib unexpectedly revealed that its thioamide derivatives demonstrated enhanced kinase inhibition and anti-tumor cell activity in vitro. Furthermore, selected thioamide derivatives exhibited improved therapeutic efficacy and reduced toxicity in mouse xenograft tumor models, indicating their potential as promising candidates for antitumor therapy.

The $LD_{50}$ value, which represents the lethal dose under which 50% of the test subjects are killed, is a crucial metric for assessing the toxicity of a drug. A lower $LD_{50}$ value indicates a higher toxicity level of the drug. Conversely, the $IC_{50}$ value, which measures the concentration of a compound required to inhibit the cell proliferation by 50%, reflects the efficacy of the compound. A higher $IC_{50}$ value suggests lower efficacy. The $LD_{50}$ and $IC_{50}$ data mentioned herein demonstrate that these compounds exhibit significantly reduced toxicity and improved efficacy compared to Capmatinib. This finding is significant as it suggests that the thioamide derivatives may offer a safer therapeutic option while maintaining or even enhancing antitumor activity.

SUMMARY

With the aim of further optimizing the toxicity and potency of the existing c-Met inhibitor, Capmatinib, the present disclosure introduces an imidazotriazine thiobenzamide derivative specifically designed for cancer therapy. Additionally, the present disclosure provides a method for the preparation of this derivative, along with its application in the treatment of cancer.

The present disclosure provides an imidazotriazine thiobenzamide derivative of formula (I), or an isomer, a pharmaceutically-acceptable salt or a prodrug thereof for cancer therapy:

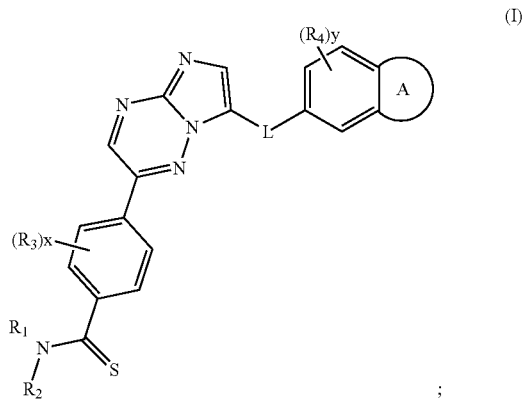

(I)

wherein in the general formula (I), the imidazotriazine thiobenzamide derivative comprises a thiobenzamide functional group.

In the general formula (I), $R_1$ and $R_2$ are independently H, hydrocarbon group with 1-15 carbons, cycloalkyl with 3-8 carbons, halogenated hydrocarbon with 1-6 halogens and 1-15 carbons, aryl group with 6-20 carbons or derivatives thereof, halogenated aryl group with 6-20 carbons or derivatives thereof, phenol with 6-20 carbons or derivatives thereof, polyphenol with 6-20 carbons or derivatives thereof, acyl group with 1-15 carbons or derivatives thereof, or 5-8 membered heterocyclic or fused heterocyclic ring with 1-4 heteroatoms or derivatives thereof; in addition, it also comprises a ring structure formed by $R_1$ and $R_2$.

In the general formula (I), $R_3$ is a substituent on the benzene ring, and x represents the number of $R_3$, which is 0, 1, 2, 3 and 4; when x=2, 3, 4, each substituent may be the same or different; $R_3$ is F, Cl, Br or I, hydroxyl or its derivatives thereof, nitro, cyan, amino or its derivatives thereof, carboxyl or its derivatives containing 1-15 carbons thereof, acyl or its derivatives containing 1-15 carbons thereof, sulfinyl or its derivatives containing 1-15 carbons thereof, sulfonyl or its derivatives containing 1-15 carbons thereof, sulfonic acid, sulfonate, sulfonic ester, phosphate group, phosphate, phosphate ester, alkyl or its derivatives containing 1-15 carbons, alkenyl or its derivatives containing 1-15 carbons, alkynyl or its derivatives containing 1-15 carbons, cycloalkyl or its derivatives containing 3-8 carbons, halogenated hydrocarbon or its derivatives containing 1-6 halogens and 1-15 carbons, halogenated alkene or its derivatives containing 1-6 halogens and 1-15 carbons, halogenated alkyne or its derivatives containing 1-6 halogens and 1-15 carbons, aryl or its derivatives containing 6-20 carbons thereof, halogenated aryl or its derivatives containing 6-20 carbons thereof, phenol or its derivatives containing 6-20 carbons thereof, polyphenol or its derivatives containing 6-20 carbons thereof, 5-8 membered heterocyclic or fused heterocyclic ring or its derivatives containing 1-4 heteroatoms thereof.

In the general formula (I), $R_4$ is a substituent on the benzene ring, and y represents the number of $R_4$, which is 0, 1, 2 or 3; when y=2 or 3, individual substituents may be the same or different; $R_4$ is F, Cl, Br or I, hydroxyl or derivative thereof, nitro, cyan, amino or its derivatives thereof, carboxyl or its derivatives containing with 1-15 carbons thereof, acyl or its derivatives containing 1-15 carbons thereof, sulfinyl or its derivatives containing 1-15 carbons thereof, sulfonyl or its derivatives containing 1-15 carbons thereof, sulfonic acid, sulfonate, sulfonic ester, phosphate group, phosphate, phosphate ester, alkyl or its derivatives containing 1-15 carbons thereof, alkenyl or its derivatives containing 1-15 carbons thereof, alkynyl or its derivatives containing 1-15 carbons thereof, cycloalkyl or its derivatives containing 3-8 carbons thereof, halogenated hydrocarbon or its derivatives containing 1-6 halogens and 1-15 carbons, halogenated alkene or its derivatives containing 1-6 halogens and 1-15 carbons, halogenated alkyne or its derivatives containing 1-6 halogens and 1-15 carbons, aryl or its derivatives containing 6-20 carbons thereof, halogenated aryl or its derivatives containing 6-20 carbons thereof, phenol or its derivatives containing 6-20 carbons thereof, polyphenol or its derivatives containing 6-20 carbons thereof, or 5-8 membered heterocyclic or fused heterocyclic ring or its derivatives containing 1-4 heteroatoms thereof.

In the general formula (I), ring A is a 4-8 membered ring with or without heteroatoms, or a derivative thereof, which is fused with the benzene ring, and is conjugated or unconjugated.

In the general formula (I), L is $CR_5R_6$, carbonyl group, imine or derivatives of imine;

wherein when L is $CR_5R_6$, $R_5$ and $R_6$ are independently H, hydrocarbon containing 1-15 carbons, hydroxyl or its derivatives thereof, amino or its derivatives thereof, halogen, cyan, carboxyl or its derivatives thereof, cycloalkyl containing 3-8 carbons, halogenated hydrocarbon containing 1-6 halogens and 1-15 carbons, aryl or its derivatives containing 6-20 carbons thereof, halogenated aryl or its derivatives containing 6-20 carbons thereof, phenol or its derivatives containing 6-20 carbons thereof, polyphenol or its derivatives containing 6-20 carbons thereof, acyl or its derivatives containing 1-15 carbons thereof, or 5-8 membered heterocyclic or fused heterocyclic ring or its derivatives containing 1-4 heteroatoms thereof; in addition, it also comprises a ring structure formed by $R_5$ and $R_6$.

In some embodiments, the imidazotriazine thiobenzamide derivative is selected from the group consisting of:

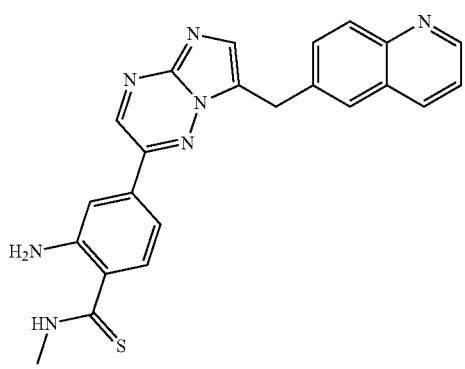
9
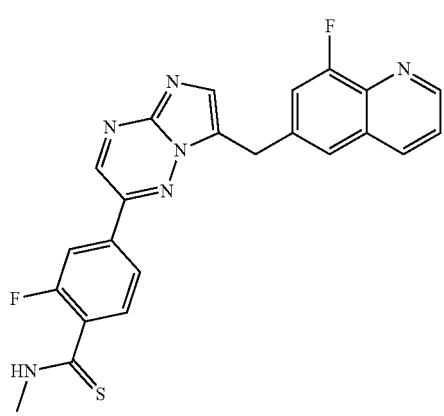
13
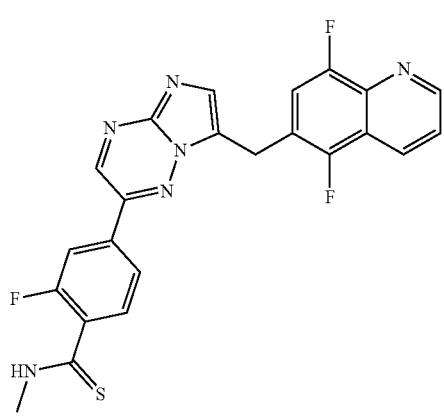
14
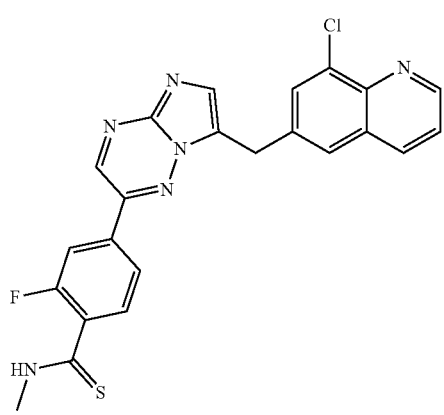
15
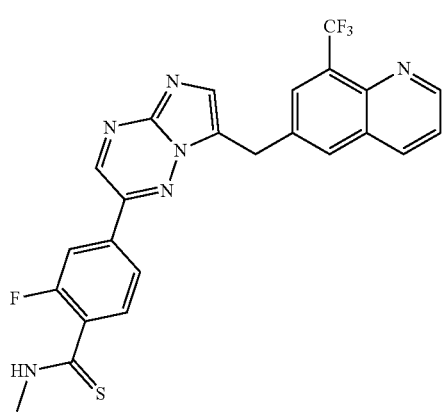
16

17
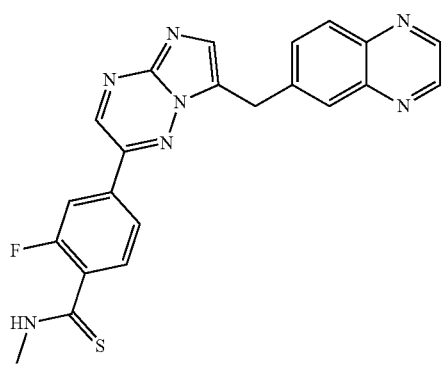
18
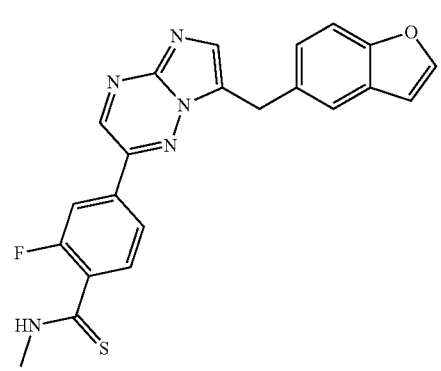
19
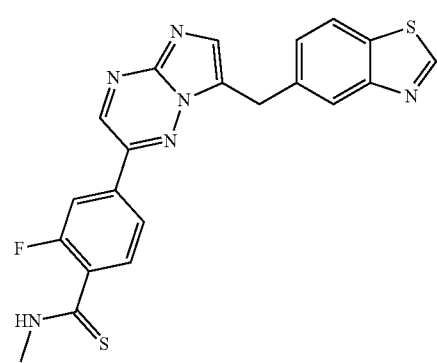
20
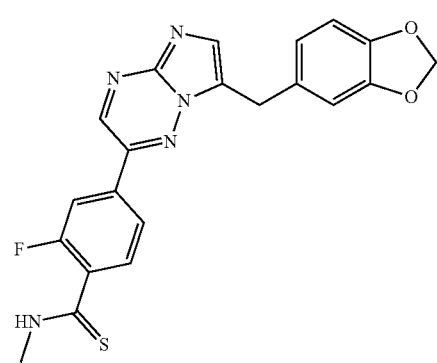
21
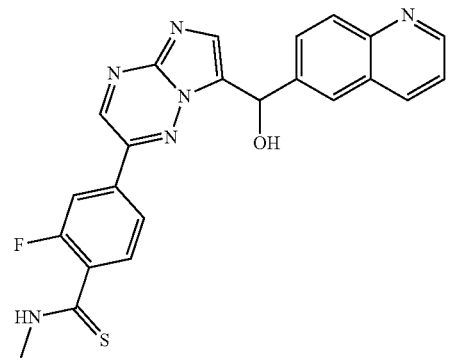
22
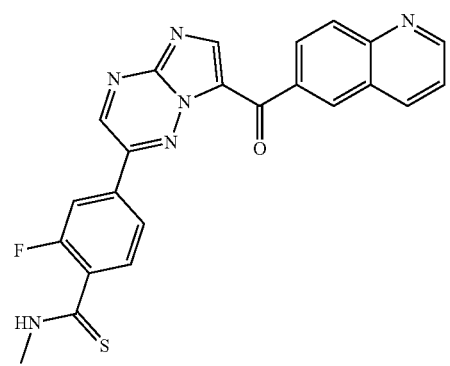
23
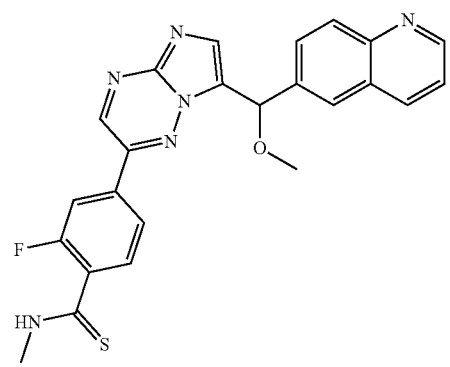
24
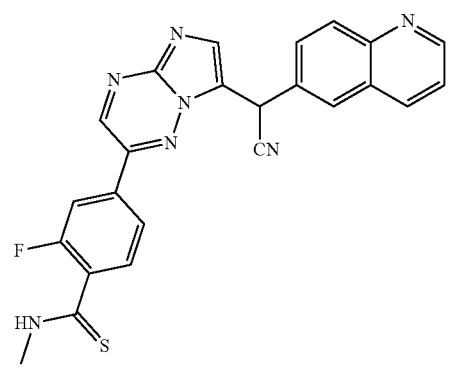

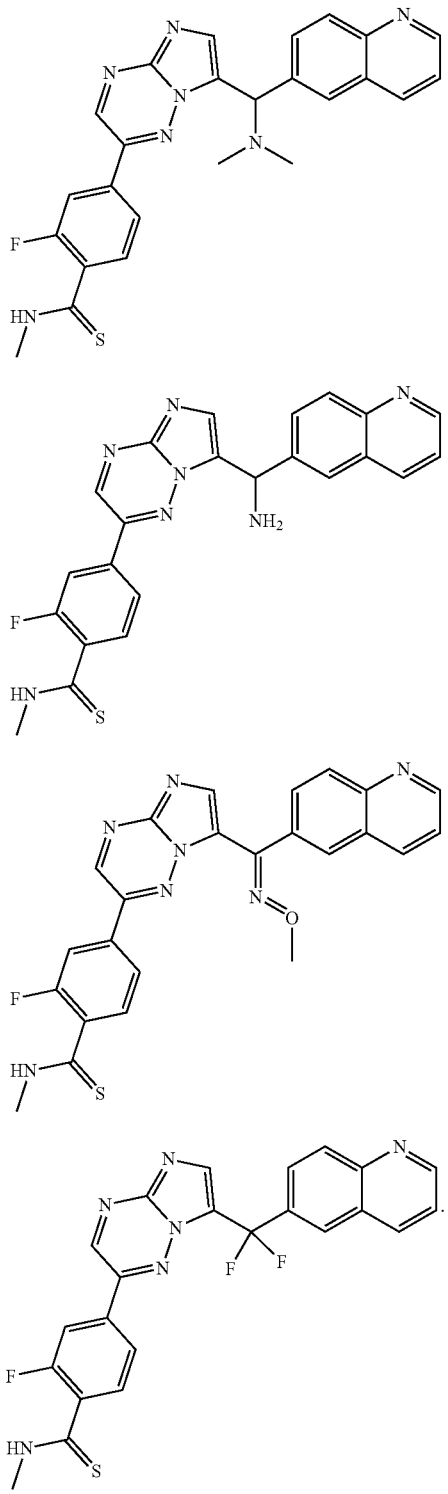

The present disclosure also provides a drug or pharmaceutical composition, comprising: a therapeutically effective amount of the imidazotriazine thiobenzamide derivative, or an isomer, a pharmaceutically-acceptable salt, or a prodrug molecule thereof; in an embodiment, the drug or the pharmaceutical composition comprises one or more of a pharmaceutically-acceptable carrier, a diluent or an excipient.

The imidazotriazine thiobenzamide derivative can be synthesized as follows:

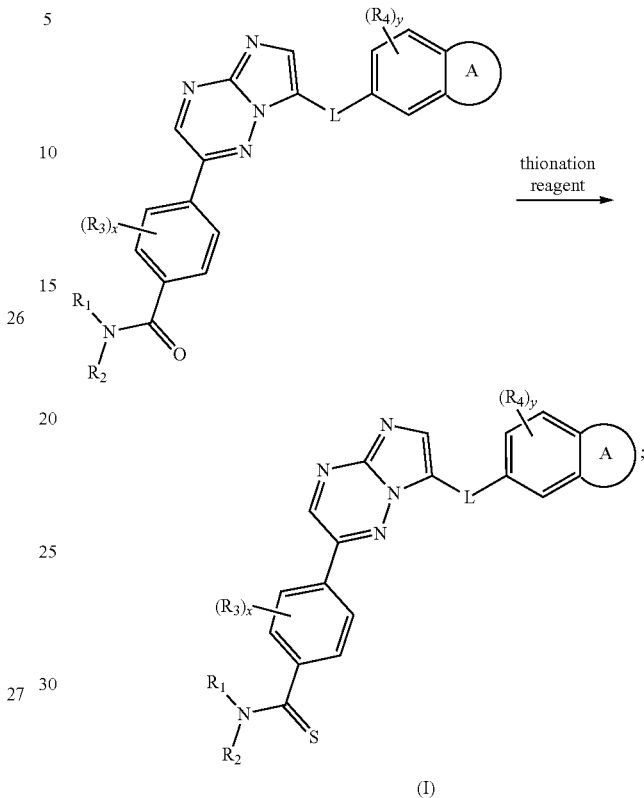

wherein the thionation reagent is phosphorus pentasulfide, Lawesson's reagent, 2,4-bis(methylthio)-1,3,2,4-dithiadiphosphetane-2,4-disulfide, 2,4-bis(phenylthio)-1,3-dithio-2,4-diphosphatidyl-2,4-disulfide, 2,4-Bis(4-phenoxyphenyl)-1,3,2,4-dithiadiphosphetane-2,4-disulfide or a mixture of any two of above; a solvent used in the thionation reaction is protonic solvent, aprotic solvent or a mixture thereof; a temperature of the thionation reaction is within a range of −78° C.-180° C.

In an embodiment, the solvent used in the thionation reaction is selected from the group consisting of dichloromethane, dichloroethane, tetrahydrofuran, acetonitrile, glycol dimethyl ether, 1,4-dioxane, N,N-dimethylformamide, dimethyl sulfoxide, and a combination thereof.

A method for treating a cancer in a subject in need thereof, wherein the cancer is selected from the group consisting of brain cancer, glioma, endometrial cancer, ovarian cancer, cervical cancer, breast cancer, colon cancer, lung cancer, prostate cancer, liver cancer, leukemia, lymphoma, skin cancer, basal cell carcinoma, hemangioma, uterine cancer, throat cancer, stomach cancer, cheilocarcinoma, esophagus cancer, nasopharyngeal carcinoma, gallbladder carcinoma, pancreatic cancer, renal carcinoma, tongue cancer, bladder cancer, melanoma, lipoma, thyroid cancer, thymic cancer and osteocarcinoma.

The imidazotriazine thiobenzamide derivative, the isomer, the pharmaceutically-acceptable salt, or the prodrug molecule is administered in combination with an antitumor drug; wherein the antitumor drug is selected from the group consisting of adriamycin, bleomycin, vinblastine, taxane, etoposide, 5-fluorouracil, cytoxan, methotrexate, cisplatin, tretinoin, temozolomide, actinomycin, imatinib, gefitinib, sorafenib, erlotinib, sunitinib, afatinib, cabozantinib, osimertinib, dabrafenib, rituximab, cetuximab, trastuzumab, nivolumab, pembrolizumab, atezolizumab, durvalumab, avelumab and a combination thereof.

The present disclosure offers several noteworthy benefits. When compared to Capmatinib, the imidazotriazine thiobenzamide derivatives described in this disclosure exhibit not only superior c-Met kinase inhibitory activity and more robust antitumor activity, but also possess the unique property of being hydrogen sulphide donors. This additional characteristic further enhances their antitumor effect while simultaneously reducing toxicity. Therefore, the imidazotriazine thiobenzamide derivatives hold promising broad application prospects in cancer therapy

DETAILED DESCRIPTION OF EMBODIMENTS

Figure 1:
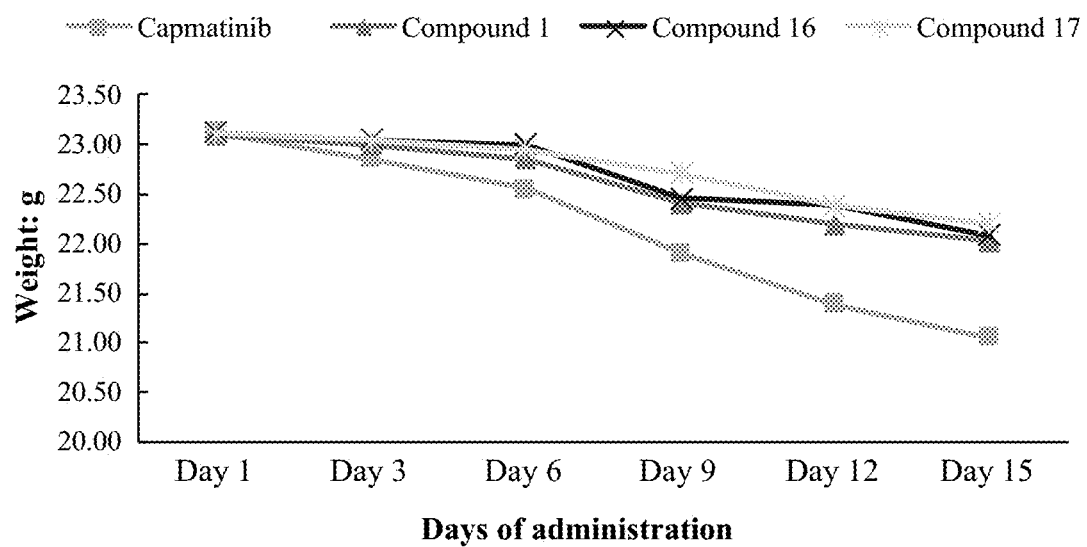
FIG. 1 shows body weight change curves of mice involved in an animal experiment according to example 13 of the present disclosure.

The present disclosure will be clearly and completely described below with reference to the accompanying drawings and embodiments. It is obvious that described herein are merely some embodiments of the present disclosure rather than all embodiments. Any other embodiments obtained by those skilled in the art based on the embodiments provided herein without making creative effort shall fall within the scope of the present disclosure.

Example 1 Preparation of Compound 1

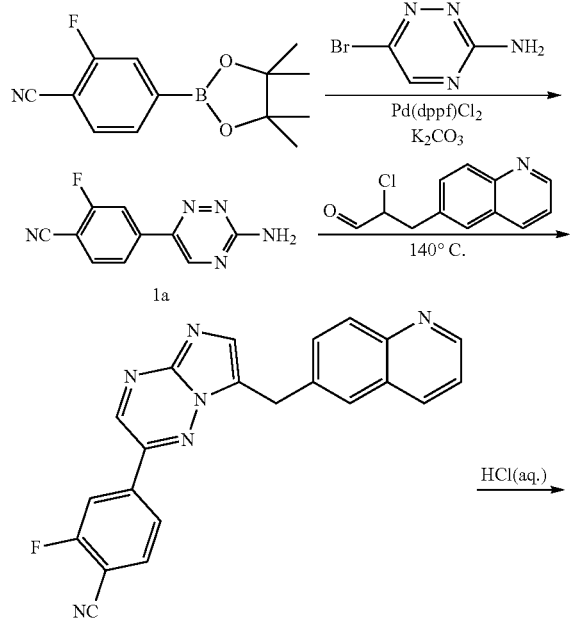

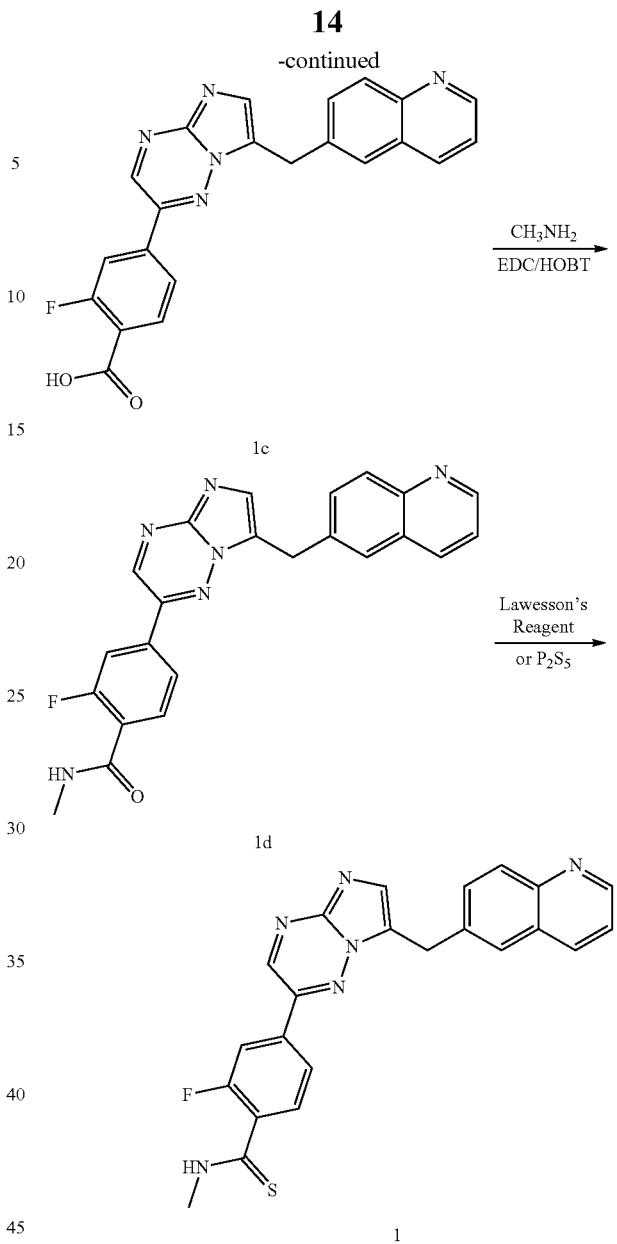

(1) Preparation of Compound 1a

Under protection of nitrogen, a reaction vessel was sequentially charged with 6-bromo-[1,2,4]-triazin-3-amine (14.0 g, 80.0 mmol), 4-cyano-3-fluorobenzeneboronic acid pinacol ester (23.7 g, 95.9 mmol), $K_2CO_3$ (49.8 g, 360.0 mmol), Pd(dppf)Cl$_2$ (2.9 g, 4.0 mmol), 170 mL of 1,4-dioxane and 85 mL of pure water. The reaction mixture was stirred at 80° C. for 3.5 h, then cooled to room temperature and filtered through a Celite pad, and the resulting filter cake was washed with 250 mL of ethyl acetate. The resultant filtrate was adjusted with 2 M dilute hydrochloric acid to pH 1-2. The organic phase was extracted twice with 250 mL of dilute hydrochloric acid. The aqueous phases were collected, and combined, and the pH was adjusted to 11-13 by slowly adding solid sodium hydroxide (NaOH) while stirring. The aqueous phase was then extracted three times with 250 mL of ethyl acetate. The resultant organic phases were combined, washed with a saturated NaCl aqueous solution, dried over anhydrous sodium sulfate, and concentrated under reduced pressure to obtain 8.2 g of gray solid product 1a (47.6% yield).

¹H-NMR (400 MHZ, DMSO-d$_6$) δ ppm: 8.93 (s, 1H), 8.12 (dd, J=11.1, 1.1 Hz, 1H), 8.07-7.99 (m, 2H), 7.70 (brs, 2H).

MS(+ESI): m/z [M+H]$^+$ 216.1.

(2) Preparation of Compound 1b

Under nitrogen protection, the compound 1a (2.5 g, 11.62 mmol), 2-chloro-3-(quinolin-6-yl)-propanal (5.3 g, 16.61 mmol) and 50 mL of glycol were sequentially added to a reaction vessel. The reaction mixture was stirred at 140° C. for 5 h, then cooled to room temperature, diluted with 300 mL of dichloromethane, and washed twice with 100 ml of water. The resultant organic phase was washed with a saturated NaCl aqueous solution, dried over anhydrous sodium sulfate, concentrated under reduced pressure, and purified by silica gel column chromatography (eluent: DCM/MeOH=50/1 to 10/1) to obtain 2.23 g of a yellow solid product 1b (50.6% yield).

¹H-NMR (400 MHZ, DMSO-d$_6$) δ ppm: 9.26 (s, 1H), 8.85 (dd, J=4.2, 1.7 Hz, 1H), 8.34-8.24 (m, 1H), 8.22-8.13 (m, 1H), 8.04 (s, 1H), 8.01-7.94 (m, 1H), 7.79 (dd, J=8.6, 2.1 Hz, 1H), 7.50 (dd, J=8.3, 4.2 Hz, 1H), 4.65 (s, 1H).

MS(+ESI): m/z [M+H]$^+$ 381.1.

(3) Preparation of Compound 1c

Under nitrogen protection, the compound 1b (450.0 mg, 1.19 mmol), 4.5 mL of concentrated hydrochloric acid, and 0.45 mL of pure water were sequentially added to a pressure-resistant glass reaction vessel. The reaction mixture was sealed and stirred at 100° C. overnight. After cooling to room temperature, 5 mL of water was added to precipitate a large amount of gray-yellow solid. The reaction mixture was continuously cooled at 0° C. for 30 min and filtered to obtain a filter cake, which was dried under reduced pressure to obtain 407 mg of a yellow solid product 1c (85.7% yield).

¹H-NMR (400 MHZ, DMSO-d$_6$) δ 9.36 ppm: 9.36 (s, 1H), 9.25 (dd, J=5.3, 1.5 Hz, 1H), 9.11 (dd, J=8.5, 1.4 Hz, 1H), 8.42 (d, J=8.8 Hz, 1H), 8.34 (d, J=1.8 Hz, 1H), 8.21 (dd, J=8.8, 1.9 Hz, 1H), 8.15 (s, 1H), 8.11-7.98 (m, 4H), 4.78 (s, 2H).

(4) Preparation of Compound 1d

Under nitrogen protection, the compound 1c (497.6 mg, 1.25 mmol), 1-hydroxybenzotriazole (HOBT) (506.7 mg, 3.75 mmol) and 25 mL of dry dichloromethane were sequentially added to a reaction vessel. The reaction mixture was stirred at room temperature. Then 1-(3-dimethylaminopropyl)-3-ethylcarbodiimide hydrochloride (EDCI) (718.8 mg, 3.75 mmol) was added and the mixture was stirred for 10 min. Subsequently, methylamine hydrochloride (253 mg, 3.75 mmol) and triethylamine (380 mg, 3.75 mmol) were added and the mixture was stirred at room temperature for 30 min. Once the reaction was completed, the reaction mixture was washed twice with 20 mL of pure water. The organic phase was washed with a saturated NaCl solution, dried over anhydrous sodium sulfate, and concentrated under reduced pressure to obtain 423 mg of a yellow solid product 1d (76.9% yield).

¹H-NMR (400 MHZ, DMSO-d$_6$) δ ppm: 9.32 (s, 1H), 9.22 (d, J=4.4 Hz, 1H), 9.04 (d, J=8.4 Hz, 1H), 8.44 (d, J=4.4 Hz, 1H), 8.34 (d, J=8.4 Hz, 1H), 8.30 (s, 1H), 8.16 (d, J=8.4 Hz, 1H), 8.00-8.12 (m, 4H), 7.82 (t, J=8.4 Hz, 1H), 4.77 (s, 2H), 2.81 (d, J=4.4 Hz, 3H).

MS(+ESI): m/z [M+H]$^+$: 413.1.

(5) Preparation of Compound 1

Under nitrogen protection, to a 50 mL pressure-resistant glass reaction vessel were sequentially added the compound 1d (256 mg, 0.62 mmol), P$_2$S$_5$-pyridine complex (376.6 mg, 1.25 mmol) and 10 mL of pyridine. The reaction vessel was then sealed, and the reaction mixture were stirred at 110° C. for 12 hours. Once the reaction was complete, the reaction mixture was cooled to room temperature, diluted with 100 mL of dichloromethane and washed four times with 50 mL of a saturated citric acid aqueous solution to remove any residual reagents or by-products. The organic phase was further washed with a saturated NaCl aqueous solution to remove any remaining water-soluble impurities. The washed organic phase was then dried over anhydrous sodium sulfate to remove any residual water. The solvent was removed under reduced pressure to concentrate the product. Finally, the concentrated product was purified by neutral alumina column chromatography using a gradient eluent of DCM/MeOH ranging from 200/1 to 100/1, resulting in the isolation of 168 mg of a yellow solid product 1 with a yield of 63.2%.

¹H-NMR (400 MHZ, DMSO-d$_6$) δ ppm: 10.62 (d, J=4.4 Hz, 1H), 9.21 (s, 1H), 8.84 (dd, J=1.6, 8.4 Hz, 1H), 8.30 (dd, J=1.6, 8.4 Hz, 1H), 7.92-8.03 (m, 5H), 7.79 (dd, J=2.0, 8.8 Hz, 1H), 7.71 (t, J=8.0 Hz, 1H), 7.50 (dd, J=4.0, 8.0 Hz, 1H), 4.63 (s, 2H), 3.16 (d, J=4.4 Hz, 3H).

MS(+ESI): m/z [M+H]$^+$: 429.1.

Example 2 Preparation of Compounds 2-20

Compounds 2-20 were synthesized following the preparation method for the compound 1 in Example 1. This process was successfully applied to the synthesis of these additional compounds, demonstrating its reproducibility and scalability.

| Compound | Structural formula | HNMR (DMSO-d$_6$) δ ppm | MS (+ESI): m/z [M + H]$^+$ |
|---|---|---|---|
| 2 | 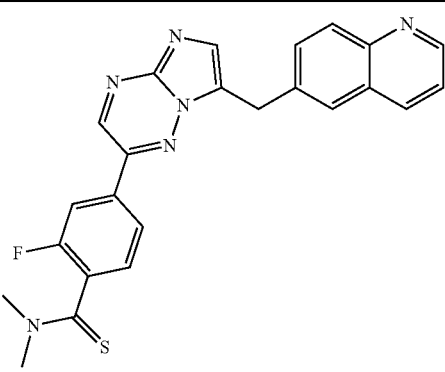 | CDCl$_3$: 8.88 (dd, J = 1.6, 4.4 Hz, 1H), 8.82 (s, 1H), 7.63-7.77 (m, 4H), 8.10 (dd, J = 1.6, 8.0 Hz, 1H), 8.07 (d, J = 8.0 Hz, 1H), 7.92 (s, 1H), 7.58 (t, J = 8.0 Hz, 1H), 7.39 (dd, J = 4.4, 8.0 Hz, 1H), 4.58 (s, 2H), 3.62 (s, 3H), 3.22 (s, 3H). | 443.1 |

| Compound | Structural formula | HNMR (DMSO-d$_6$) δ ppm | MS (+ESI): m/z [M + H]$^+$ |
|---|---|---|---|
| 3 | | 10.49 (d, J = 8.0 Hz, 1H), 9.20 (s, 1H), 8.84 (dd, J = 1.6, 8.4 Hz, 1H), 8.30 (dd, J = 1.6, 8.4 Hz, 1H), 7.93-8.03 (m, 5H), 7.79 (dd, J = 2.0, 8.8 Hz, 1H), 7.64 (t, J = 8.0 Hz, 1H), 7.50 (dd, J = 4.0, 8.0 Hz, 1H), 4.57-4.69 (m, 3H), 1.26 (d, J = 6.4 Hz, 6H). | 457.2 |
| 4 | | 10.13 (d, J = 4.4 Hz, 1H), 9.23 (s, 1H), 8.81 (dd, J = 1.6, 8.4 Hz, 1H), 8.31 (dd, J = 1.6, 8.4 Hz, 1H), 7.90-8.10 (m, 5H), 7.75 (dd, J = 2.0, 8.8 Hz, 1H), 7.68 (t, J = 8.0 Hz, 1H), 7.38 (dd, J = 4.0, 8.0 Hz, 1H), 4.62-4.89 (m, 1H), 4.61 (s, 2H), 1.35-1.46 (m, 4H). | 455.1 |
| 5 | | 10.55 (dd, J = 4.4, 9.2 Hz, 1H), 8.92 (d, J = 2.4 Hz, 1H), 8.84 (dd, J = 1.6, 4.0 Hz, 1H), 8.30 (dd, J = 0.8, 8.4 Hz, 1H), 8.01 (s, 1H), 7.97 (d, J = 8.4 Hz, 1H), 7.92 (d, J = 1.6 Hz, 1H), 7.88 (d, J = 8.4 Hz, 1H), 7.81 (s, 1H), 7.76-7.80 (m, 2H), 7.49 (dd, J = 4.4, 8.0 Hz, 1H), 4.60 (s, 2H), 3.18 (d, J = 4.4 Hz, 3H). | 429.1 |
| 6 | | 10.71 (d, J = 3.2 Hz, 1H), 8.92 (s, 1H), 8.84 (d, J = 4.4 Hz, 1H), 8.28 (d, J = 8.0 Hz, 1H), 8.04 (s, 1H), 7.88-8.00 (m, 2H), 7.66-7.80 (m, 2H), 7.56-7.64 (m, 1H), 7.46-7.54 (m, 1H), 4.62 (s, 2H), 3.16 (d, J = 3.2 Hz, 3H). | 447.1 |

-continued

| Compound | Structural formula | HNMR (DMSO-d$_6$) δ ppm | MS (+ESI): m/z [M + H]$^+$ |
|---|---|---|---|
| 7 | | 10.77 (d, J = 3.2 Hz, 1H), 8.93 (s, 1H), 8,84 (d, J = 4.4 Hz, 1H), 8.28 (d, J = 8.0, 1H), 8.04 (s, 1H), 7.96 (d, J = 8.0, 1H), 7.90 (s, 1H), 7.76 (d, J = 8.0, 1H), 7.65-7.73 (m, 1H), 7.45-7.55 (m, 2H), 4.59 (s, 2H), 3.16 (d, J = 3.2 Hz, 3H). | 447.1 |
| 8 | | 10.58 (d, J = 4.4 Hz, 1H), 9.23 (s, 1H), 8.84 (dd, J = 1.6, 8.4 Hz, 1H), 8.29 (dd, J = 1.6, 8.0 Hz, 1H), 7.88-8.05 (m, 5H), 7.79 (dd, J = 1.6, 8.0 Hz, 1H), 7.75 (d, J = 8.0 Hz, 1H), 7.55 (dd, J = 4.0, 8.0 Hz, 1H), 4.61 (s, 2H), 3.12 (d, J = 4.4 Hz, 3H). | 445.1 |
| 9 | | 10.27 (d, J = 4.8 Hz, 1H), 9.15 (s, 1H), 8.78 (dd, J = 1.6, 8.0 Hz, 1H), 8.32 (dd, J = 1.6, 4.0 Hz, 1H), 8.22 (dt, J = 1.2, 8.0 Hz, 1H), 7.96 (s, 1H), 7.91-7.99 (m, 2H), 7.50-75 (m, 3H), 7.68 (dd, J = 1.6, 8.8 Hz, 1H), 7.61-7.65 (m, 2H), 4.64 (s, 2H), 3.12 (d, J = 4.8 Hz, 3H). | 426.1 |
| 10 | | 10.26 (d, J = 4.8 Hz, 1H), 9.22 (s, 1H), 8.83 (dd, J = 1.6, 8.0 Hz, 1H), 8.38 (dd, J = 1.6, 4.0 Hz, 1H), 8.29 (dt, J = 1.2, 8.0 Hz, 1H), 8.03 (s, 1H), 7.92-7.98 (m, 2H), 7.79 (dd, J = 2.0, 8.8 Hz, 1H), 7.71 (dd, J = 1.6, 8.8 Hz, 1H), 7.60-7.65 (m, 2H), 4.63 (s, 2H), 3.82 (s, 3H), 3.12 (d, J = 4.8 Hz, 3H). | 440.2 |

| Compound | Structural formula | HNMR (DMSO-d$_6$) δ ppm | MS (+ESI): m/z [M + H]$^+$ |
| --- | --- | --- | --- |
| 11 | | 12.96 (s, 1H), 10.17 (s, 1H), 9.12 (q, J = 4.4 Hz, 1H), 8.84 (dd, J = 4.2, 1.7 Hz, 1H), 8.39 (dd, J = 8.4, 1.7 Hz, 1H), 8.03-7.92 (m, 4H), 7.79 (dd, J = 8.7, 2.0 Hz, 1H), 7.67 (d, J = 1.8 Hz, 1H), 7.63 (dd, J = 8.3, 1.8 Hz, 1H), 7.49 (dd, J = 8.3, 4.2 Hz, 1H), 4.62 (s, 2H), 3.11 (d, J = 4.4 Hz, 3H). | 427.1 |
| 12 | | 10.26 (d, J = 4.8 Hz, 1H), 9.22 (s, 1H), 8.83 (dd, J = 1.6, 8.0 Hz, 1H), 8.38 (dd, J = 1.6, 4.0 Hz, 1H), 8.29 (dt, J = 1.2, 8.0 Hz, 1H), 8.03 (s, 1H), 7.92-7.98 (m, 2H), 7.79 (dd, J = 2.0, 8.8 Hz, 1H), 7.71 (dd, J = 1.6, 8.8 Hz, 1H), 7.60-7.65 (m, 2H), 4.63 (s, 2H), 3.82 (s, 3H), 3.12 (d, J = 4.8 Hz, 3H). | 441.1 |
| 13 | | 10.62 (s, 1H), 9.22 (s, 1H), 8.89 (dd, J = 1.6, 4.0 Hz, 1H), 8.38 (dt, J = 1.6, 8.4 Hz, 1H), 7.98-8.04 (m, 3H), 7.80 (s, 1H), 7.64-7.73 (m, 2H), 7.60 (dd, J = 4.0, 8.4 Hz, 1H), 4.64 (s, 2H), 3.15 (s, 3H). | 447.1 |
| 14 | | 10.62 (d, J = 4.4 Hz, 1H), 9.22 (s, 1H), 8.99 (dd, J = 1.6, 4.0 Hz, 1H), 8.55 (dt, J = 1.6, 8.4 Hz, 1H), 7.98-8.03 (m, 3H), 7.67-7.76 (m, 3H), 4.64 (s, 2H), 3.16 (d, J = 4.4 Hz, 3H). | 465.1 |

-continued

| Compound | Structural formula | HNMR (DMSO-d$_6$) δ ppm | MS (+ESI): m/z [M + H]$^+$ |
|---|---|---|---|
| 15 | | 10.61 (d, J = 4.4 Hz, 1H), 9.24 (s, 1H), 8.89 (dd, J = 1.6, 4.0 Hz, 1H), 8.38 (dt, J = 1.6, 8.4 Hz, 1H), 7.96-8.04 (m, 3H), 7.84 (s, 1H), 7.62-7.75 (m, 2H), 7.60 (dd, J = 4.0, 8.4 Hz, 1H), 4.71 (s, 2H), 3.19 (d, J = 4.4 Hz, 3H). | 463.1 |
| 16 | | 10.66 (d, J = 4.4 Hz, 1H), 9.25 (s, 1H), 8.85 (dd, J = 1.6, 8.4Hz, 1H), 8.35 (d, J = 8.4 Hz, 1H), 7.90-8.05 (m, 5H), 7.73 (d, J = 8.4 Hz, 1H), 7.52 (dd, J = 4.0, 8.4 Hz, 1H), 4.67 (s, 2H), 3.18 (d, J = 4.4 Hz, 3H). | 497.1 |
| 17 | | 10.61 (d, J = 4.4 Hz, 1H), 9.35 (s, 1H), 8.88-8.74 (m, 2H), 8.01-8.05 (m, 2H), 7.92 (s, 1H), 7.70-7.65 (m, 3H), 7.50 (dd, J = 4.0, 8.0 Hz, 1H), 4.58 (s, 2H), 3.15 (d, J = 4.4 Hz, 3H). | 430.1 |
| 18 | | CDCl$_3$: 8.67 (brs, 1H), 8.63 (s, 1H), 8.10 (t, J = 8.0 Hz, 1H), 7.80 (s, 1H), 7.56-7.64 (m, 3H), 7.53 (dd, J = 1.6, 12.0 Hz, 1H), 7.47 (d, J = 8.0 Hz, 1H), 7.28 (dd, J = 1.6, 12.0 Hz, 1H), 6.72 (dd, J = 1.0, 2.0 Hz, 1H), 4.44 (s, 2H), 3.42 (d, J = 4.8 Hz, 3H). | 418.1 |

-continued

| Compound | Structural formula | HNMR (DMSO-d$_6$) δ ppm | MS (+ESI): m/z [M + H]$^+$ |
|---|---|---|---|
| 19 | | 10.62 (d, J = 4.4 Hz, 1H), 9.36 (s, 1H), 9.20 (s, 1H), 8.08-8.14 (m, 2H), 8.02-8.06 (m, 2H), 7.98 (s, 1H), 7.71 (t, J = 8.0 HZ, 1H), 7.54 (dd, J = 4.0, 8.0 Hz, 1H), 4.60 (s, 2H), 3.16 (d, J = 4.4 Hz, 3H). | 435.1 |
| 20 | | 10.65 (d, J = 4.4 Hz, 1H), 9.31 (s, 1H), 8.85 (dd, J = 1.6, 8.4 Hz, 1H), 8.32 (dd, J = 1.6, 8.4 Hz, 1H), 7.82-7.91 (m, 1H), 7.91 (s, 1H), 6.60-7.12 (m, 3H), 6.12 (s, 2H), 4.61 (s, 2H), 3.14 (d, J = 4.4 Hz, 3H). | 422.1 |

Example 3 Preparation of Compounds 21-22

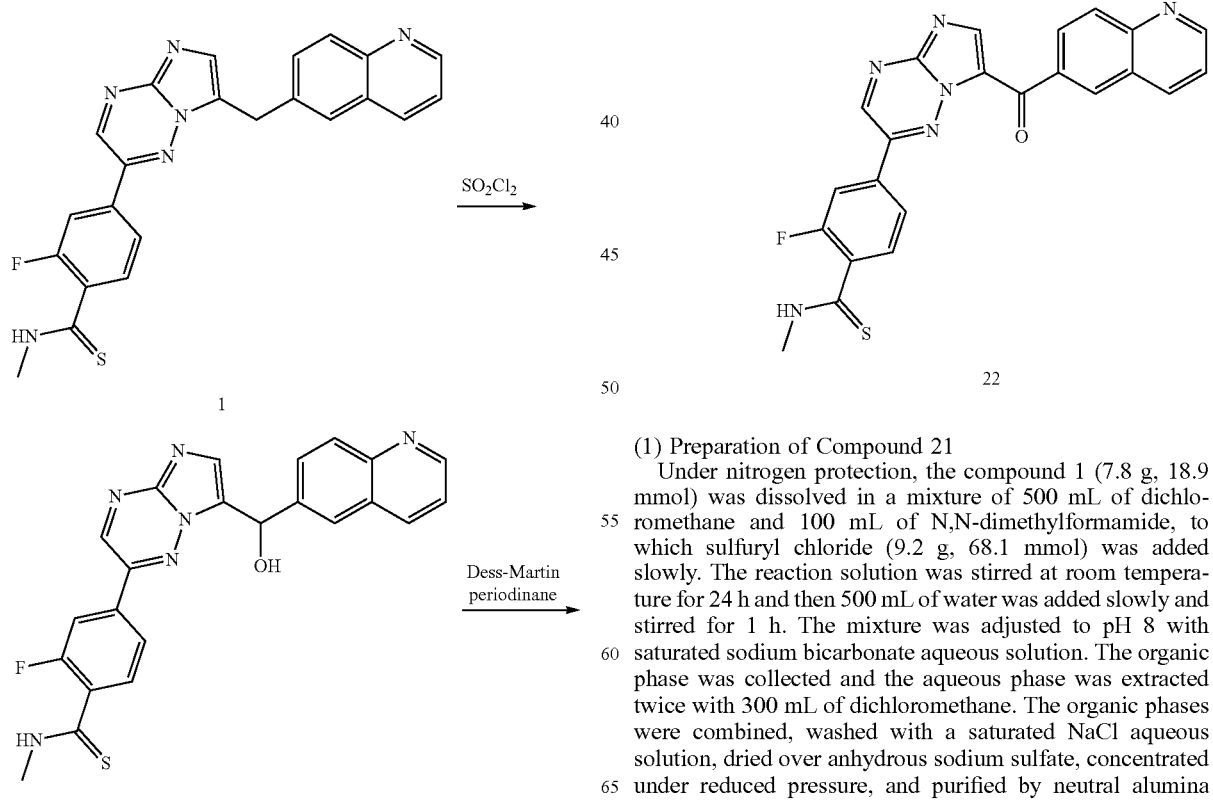

(1) Preparation of Compound 21

Under nitrogen protection, the compound 1 (7.8 g, 18.9 mmol) was dissolved in a mixture of 500 mL of dichloromethane and 100 mL of N,N-dimethylformamide, to which sulfuryl chloride (9.2 g, 68.1 mmol) was added slowly. The reaction solution was stirred at room temperature for 24 h and then 500 mL of water was added slowly and stirred for 1 h. The mixture was adjusted to pH 8 with saturated sodium bicarbonate aqueous solution. The organic phase was collected and the aqueous phase was extracted twice with 300 mL of dichloromethane. The organic phases were combined, washed with a saturated NaCl aqueous solution, dried over anhydrous sodium sulfate, concentrated under reduced pressure, and purified by neutral alumina column chromatography (eluent: DCM/MeOH=40/1) to obtain 1.5 g of a yellow solid product 21 (21.0% yield).

$^1$H-NMR (400 MHZ, DMSO-d$_6$) δ ppm: 10.63 (d, J=4.8 Hz, 1H), 9.21 (s, 1H), 8.87 (dd, J=1.6, 8.4 Hz, 1H), 8.34 (dd, J=1.6, 8.4 Hz, 1H), 7.95-8.06 (m, 5H), 7.89 (dd, J=2.0, 8.8 Hz, 1H), 7.83 (t, J=8.0 Hz, 1H), 7.50 (dd, J=4.0, 8.0 Hz, 1H), 6.57 (dd, J=4.8, 9.6 Hz, 2H), 3.16 (d, J=4.8 Hz, 3H).

MS(+ESI): m/z [M+H]$^+$: 445.1.

(2) Preparation of Compound 22

Under nitrogen protection, the compound 21 (351 mg, 0.82 mmol) was dissolved in 300 mL of anhydrous dichloromethane (DCM), then Dess-Martin regent (3.48 g, 8.2 mmol) was added. The reaction mixture was stirred at room temperature for 3 h. Once the reaction was completed, 200 mL of ice water was added to quench the reaction. The organic phase was collected and the aqueous phase was extracted twice with 150 mL of dichloromethane. The organic phases were combined, washed with saturated NaCl aqueous solution, dried over anhydrous sodium sulfate, concentrated under reduced pressure, and purified by neutral alumina column chromatography (eluent: DCM/MeOH=50/1) to obtain 200 mg of a yellow solid product 22 (57.2% yield).

$^1$H-NMR (400 MHZ, DMSO-d$_6$) δ ppm: 10.68 (d, J=4.8 Hz, 1H), 9.26 (s, 1H), 8.35-8.56 (m, 3H), 8.00-8.17 (m, 4H), 7.98-8.14 (m, 2H), 7.76 (dd, J=4.0, 8.0 Hz, 1H), 3.15 (d, J=4.8 Hz, 3H).

MS(+ESI): m/z [M+H]$^+$: 443.1.

Example 4 Preparation of Compound 23

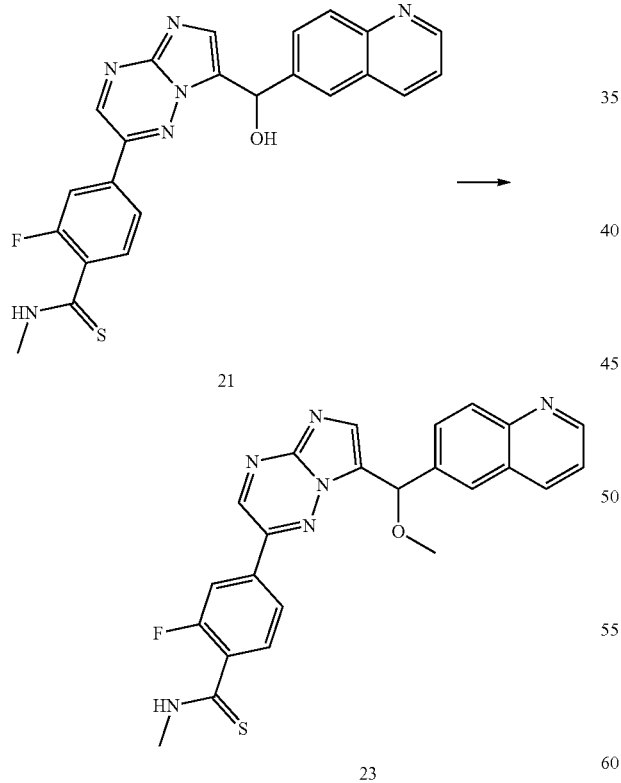

Under nitrogen protection, the compound 21 (100 mg, 0.225 mmol) was dissolved in 10 mL of N,N-dimethylformamide. Subsequently, cesium carbonate (152 mg, 0.467 mmol) and dimethyl sulfate (58.8 mg, 0.467 mmol) were added. The reaction mixture was stirred at 80° C. for 8 h, and then cooled to room temperature. Subsequently, 50 mL of saturated ammonium chloride aqueous solution was added, and the aqueous phase was extracted three times with 50 mL of dichloromethane. The organic phases were combined, washed with saturated NaCl aqueous solution, dried over anhydrous sodium sulfate, concentrated under reduced pressure, and purified with neutral alumina column chromatography (eluent: DCM/MeOH=100/1 to 50/1) to obtain 27 mg of a yellow solid product 23 (26.2% yield).

$^1$H-NMR (400 MHZ, DMSO-d$_6$) δ ppm: 10.53 (d, J=4.4 Hz, 1H), 9.17 (s, 1H), 8.45-8.56 (m, 2H), 8.31-8.36 (m, 1H), 8.20-8.27 (m, 3H), 7.99 (s, 1H), 7.94 (dd, J=2.0, 8.8 Hz, 1H), 7.87-7.94 (m, 1H), 7.66 (dd, J=4.0, 8.0 Hz, 1H), 6.35 (s, 1H), 3.47 (s, 3H), 3.24 (d, J=4.4 Hz, 3H).

MS(+ESI): m/z [M+H]$^+$: 459.1.

Example 5 Preparation of Compound 24

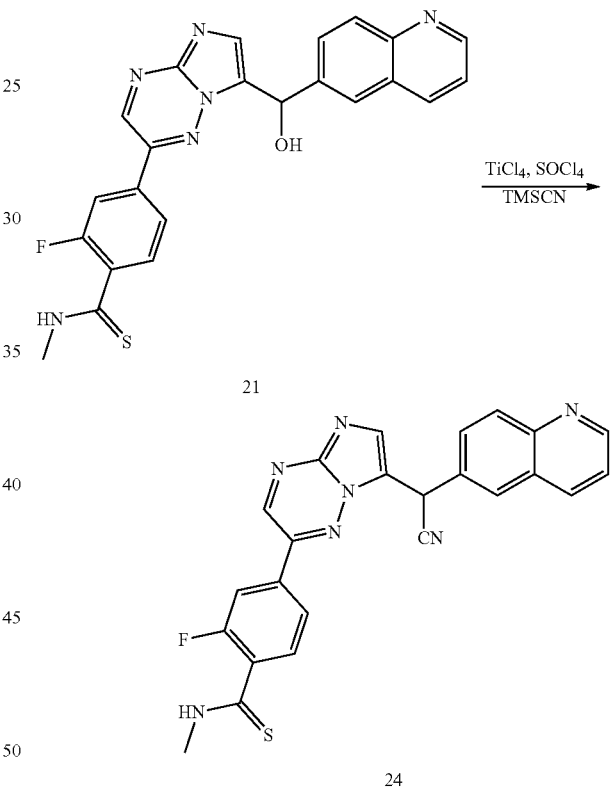

Under nitrogen protection, the compound 21 (1.0 g, 2.33 mmol) was dissolved in 100 mL of anhydrous dichloromethane. Thionyl chloride (0.417 g, 3.504 mmol) was then added and the reaction mixture was stirred at room temperature for 2 h. Trimethylsilyl cyanide (0.232 g, 2.30 mmol) and titanium tetrachloride (0.443 g, 2.33 mmol) were added and stirred for another 2 h. The mixture was then concentrated under reduced pressure. 50 mL of water was added to the residue, and then extracted three times with 50 mL of ethyl acetate each time. The organic phases were combined, dried over anhydrous sodium sulfate, and purified with silica gel column chromatography (eluent: DCM/MeOH=100/1 to 50/1) to obtain 148 mg of a white solid product 24 (14.4% yield).

¹H-NMR (400 MHZ, DMSO-d₆) δ ppm: 10.65 (d, J=4.4 Hz, 1H), 9.14 (s, 1H), 8.45-8.56 (m, 2H), 8.31-8.36 (m, 1H), 8.20-8.27 (m, 3H), 7.99 (s, 1H), 7.91 (dd, J=2.0, 8.8 Hz, 1H), 7.78-7.85 (m, 1H), 7.65 (dd, J=4.0, 8.0 Hz, 1H), 6.95 (s, 1H), 3.16 (d, J=4.4 Hz, 3H).

MS(+ESI): m/z [M+H]⁺: 454.1

Example 6 Preparation of Compound 25

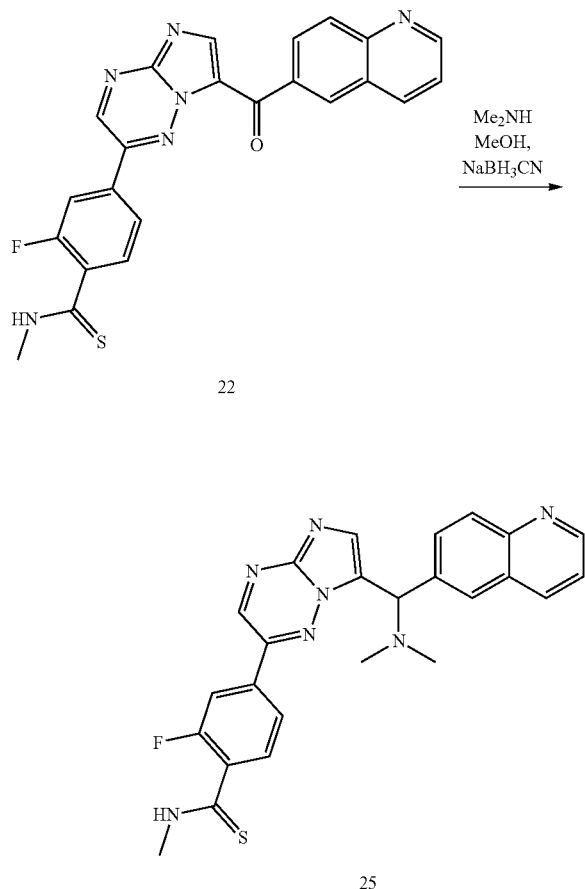

The compound 22 (1.0 g, 2.26 mmol) was dissolved in 20 mL of methyl alcohol, to which methylamine hydrochloride (0.153 g, 2.26 mmol) was added. The reaction mixture was stirred at room temperature for 4 h and then sodium cyanoborohydride (0.142 g, 2.26 mmol) was added. After stirring for 1 h, the reaction mixture was diluted with 50 mL of ethyl acetate and washed twice with 50 mL of 10% potassium fluoride aqueous solution each time. The organic phase was dried over anhydrous sodium sulfate, concentrated, and purified by neutral alumina column chromatography (eluent: DCM/MeOH=100/1 to 50/1) to obtain 482 mg of a white solid compound 25 (45.2% yield).

¹H-NMR (400 MHZ, DMSO-d₆) δ ppm: 10.63 (d, J=4.4 Hz, 1H), 9.15 (s, 1H), 8.36-8.50 (m, 3H), 8.21-8.28 (m, 3H), 7.98 (s, 1H), 7.95 (dd, J=2.0, 8.8 Hz, 1H), 7.81-7.88 (m, 1H), 7.57 (dd, J=4.0, 8.0 Hz, 1H), 6.75 (s, 1H), 3.18 (d, J=4.4 Hz, 3H), 2.36 (s, 6H).

MS(+ESI): m/z [M+H]⁺: 472.2

Example 7 Preparation of Compound 26

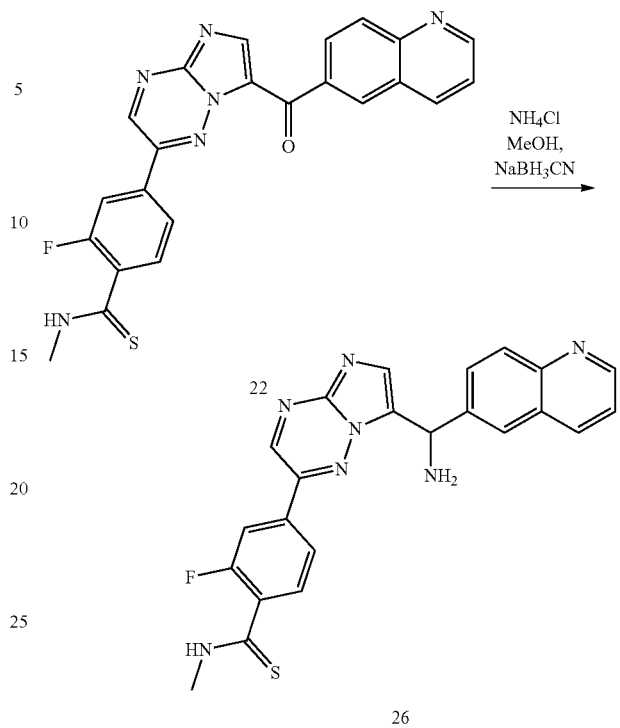

The compound 22 (1.0 g, 2.26 mmol) was dissolved in 20 mL of methyl alcohol, to which ammonium chloride (0.121 g, 2.26 mmol) was added. The reaction mixture was stirred at room temperature for 4 h and then sodium cyanoborohydride (0.142 g, 2.26 mmol) was added. After stirring for 1 h, the mixture was diluted with 50 mL of ethyl acetate and washed twice with 50 mL of 10% potassium fluoride aqueous solution each time. The organic phase was dried over anhydrous sodium sulfate, concentrated, and purified with neutral alumina column chromatography (eluent: DCM/MeOH=100/1 to 40/1) to obtain 350 mg of a white solid compound 26 (34.9% yield).

¹H-NMR (400 MHZ, DMSO-d₆) δ ppm: 10.54 (d, J=4.8 Hz, 1H), 9.16 (s, 1H), 8.84 (dd, J=1.6, 8.4 Hz, 1H), 8.31 (dd, J=1.6, 8.4 Hz, 1H), 7.93-8.04 (m, 5H), 7.83 (dd, J=2.0, 8.8 Hz, 1H), 7.73 (t, J=8.0 Hz, 1H), 7.50 (dd, J=4.0, 8.0 Hz, 1H), 5.20 (s, 2H), 6.15-6.20 (m, 1H), 3.24 (d, J=4.4 Hz, 3H).

MS(+ESI): m/z [M+H]⁺: 444.1.

Example 8 Preparation of Compound 27

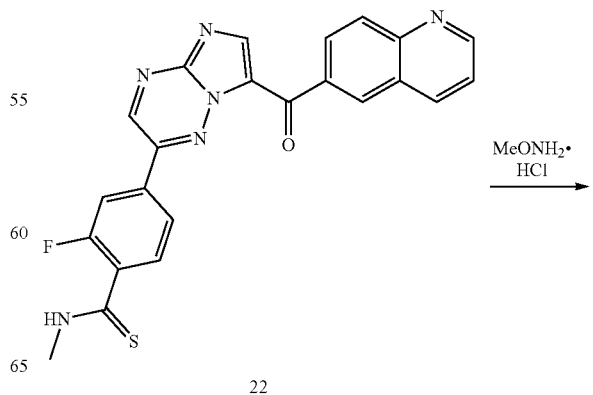

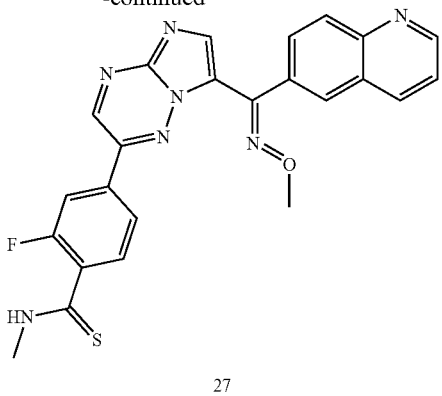

27

The compound 22 (1.0 g, 2.26 mmol), methoxylamine hydrochloride (0.468 g, 5.60 mmol), anhydrous sodium acetate (1.23 g, 9.04 mmol), 20 mL of methyl alcohol and 20 mL of water were added to a pressure-resistant glass reaction tube. The reaction tube was sealed, and the mixture was stirred and refluxed for 4 h. After being cooled to room temperature, the reaction mixture was extracted three times each with 40 mL of dichloromethane. The organic phases were combined, dried over anhydrous sodium sulfate, concentrated, and purified with silica gel column chromatography (eluent: DCM/MeOH=50/1) to obtain 799 mg of a white solid compound 27 (75.0% yield).

$^{1}$H-NMR (400 MHZ, DMSO-d$_6$) δ ppm: 10.64 (d, J=4.8 Hz, 1H), 9.26 (s, 1H), 8.32-8.53 (m, 3H), 8.01-8.08 (m, 3H), 7.98 (s, 1H), 7.91 (dd, J=2.0, 8.8 Hz, 1H), 7.71-7.79 (m, 2H), 3.88 (s, 3H), 3.14 (d, J=4.8 Hz, 3H).

MS(+ESI): m/z [M+H]$^+$: 472.1.

Example 9 Preparation of Compound 28

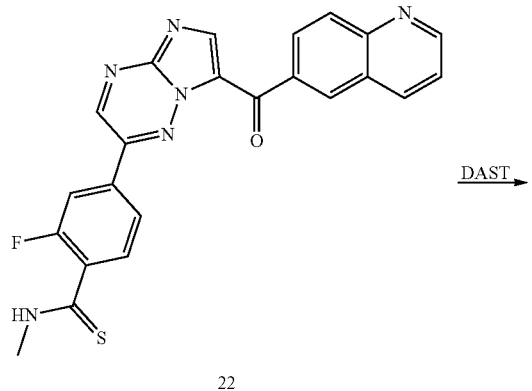

Under nitrogen protection, the compound 22 (1.0 g, 2.26 mmol) was dissolved in 50 mL of dichloromethane. Diethylaminosulphur trifluoride (DAST) (806 mg, 5.0 mmol) was then added at 0° C. The reaction mixture was stirred at room temperature for 12 h. Once the reaction was completed, 50 mL of water was added to quench the reaction. The organic phase was collected, and the aqueous phase was extracted twice each with 30 mL of dichloromethane. The organic phases were combined, dried over anhydrous sodium sulfate, and purified with silica gel column chromatography (eluent: DCM/MeOH=50/1) to obtain 640 mg of a white solid compound 28 (61.0% yield).

$^{1}$H-NMR (400 MHZ, DMSO-d$_6$) δ ppm: 10.84 (d, J=4.8 Hz, 1H), 9.33 (s, 1H), 8.32-8.53 (m, 3H), 8.01-8.28 (m, 3H), 8.01 (s, 1H), 7.95-8.01 (m, 2H), 7.68 (dd, J=4.0, 8.0 Hz, 1H), 3.32 (d, J=4.4 Hz, 3H).

MS(+ESI): m/z [M+H]: 465.1.

Example 10 Measure the LD$_{50}$ of Compounds 1-28

Experimental objective: Evaluating toxicities of compounds by measuring LD$_{50}$ of the compounds 1-28.

Experimental methods: Specific pathogen free (SPF) Kunming mice were selected, which were in outbred stock, half male and half female, and weighing 20±2 g. First, a preliminary experiment was conducted to explore the dose range for each compound. Then formal experiments were carried out. Within the range of lethal doses of 0%-100% obtained by the preliminary experiments, 5 doses were selected to increase or decrease in equal geometric progression, ensuring that half of the groups had a death rate above 50% and the other half had a death rate below 50%. After animals were divided into different groups and the dosage was calculated, drugs were intragastrically administered in each group. Duration from administration to the occurrence of a toxic response, symptoms and their sequence, time of the occurrence of death, concentration time of death, and time of the death of the last mouse were recorded. Additionally, the number of deaths in each group was recorded day by day. Based on the experimental data, LD$_{50}$ was calculated by Bliss calculation method.

Experimental results are shown in Table 1.

TABLE 1

The LD$_{50}$ of compounds 1-28

| Compound | LD$_{50}$(mg/KG) |
|---|---|
| 1 | 293 |
| 2 | 284 |
| 3 | 291 |
| 4 | 320 |
| 5 | 298 |
| 6 | 292 |
| 7 | 305 |
| 8 | 321 |
| 9 | 297 |
| 10 | 292 |
| 11 | 296 |
| 12 | 286 |
| 13 | 314 |
| 14 | 291 |
| 15 | 305 |
| 16 | 296 |
| 17 | 318 |
| 18 | 302 |
| 19 | 297 |
| 20 | 305 |
| 21 | 298 |
| 22 | 289 |

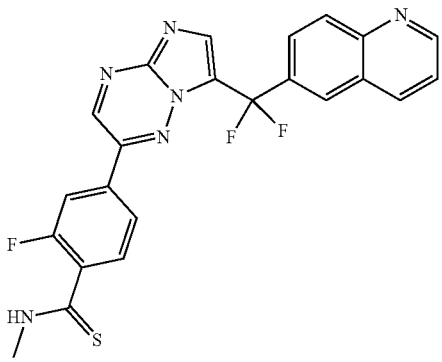

TABLE 1-continued

The $LD_{50}$ of compounds 1-28

| Compound | $LD_{50}$(mg/KG) |
|---|---|
| 23 | 320 |
| 24 | 296 |
| 25 | 287 |
| 26 | 295 |
| 27 | 310 |
| 28 | 294 |
| Capmatinib | 164 |

Referring to the experimental results, the $LD_{50}$ values of the compounds 1-28 were higher than that of Capmatinib, which indicated that compounds 1-28 have lower toxicities compared to Capmatinib.

Example 11 The c-MET Inhibitory Activity

Experimental objective: Evaluating c-MET inhibitory activities of the compounds

Experimental methods: Enzyme reaction substrate, poly (Glu, Tyr)sodium salt (Glu:Tyr=4:1) was diluted with potassium-free phosphate buffered saline (PBS) (10 mM sodium phosphate buffer, 150 mM NaCl, pH=7.2-7.4) to 20 μg/mL, coated on an ELISA plate with a volume of 125 μL/well, and reacted at 37° C. for 12 h. The supernatant in each well was discarded, and the ELISA plate was washed with 200 μL/well T-PBS (potassium-free PBS containing 0.1% Tween-20) three times for 5 minutes each time. Then the ELISA plate was dried in an oven at 37° C. for 2 h.

The maximum concentration of compounds was set to 3.0 μM, and the compound solution was subjected to 3-fold dilution with DMSO, a total of 10 concentration levels were obtained as follows: 3.0 μM, 1.0 μM, 0.33 μM, 0.11 μM, 0.037 μM, 0.012 μM, 0.0041 μM, 0.0014 μM, 0.00045 μM and 0.00015 μM. Each concentration was tested in triplicate. 80 μL of Adenosine Triphosphate (ATP) solution diluted with reaction buffer, 10 μL of compounds with various concentrations (10 μL blank DMSO solution was added to a negative control well) and 10 μL of enzyme solution diluted with reaction buffer were sequentially added into each well. The mixture was then processed on a shaker at 37° C. for 1 h. The final reaction buffer contained HEPES (pH=7.4) 50 mM, $MgCl_2$ 50 mM, $MnCl_2$ 0.5 mM, $Na_3VO_4$ 0.2 mM and DTT 1 mM. The final concentration of the ATP solution was 4 μM, and the amount of enzyme was 1 μL/well. The ELISA plate was washed three times with T-PBS.

Antibody PY99, which was diluted to 0.4 μg/mL with 5 mg/mL T-PBS containing bovine serum albumin (BSA), was added into the plate with the volume of 100 μL/well. The ELISA plate was shaken at 37° C. for 0.5 h, and washed three times with T-PBS.

Goat-Anti-Mouse (IgG), which was labeled with horseradish peroxidase (HRP) was diluted to 0.5 μg/mL with 5 mg/mL T-PBS containing BSA and was added into the plate with the volume of 100 μL/well. The plate was shaken at 37° C. for 0.5 h and washed three times with T-PBS.

The o-phenylenediamine (OPD) color development solution (2 mg/mL), which was diluted with 0.1 M of citric acid-sodium citrate buffer (pH=5.4) containing 0.03% $H_2O_2$, was added into the plate (100 μL/well) and reacted at 25° C. in the dark for 5 min.

The reaction was terminated with 2 M $H_2SO_4$ solution (50 μL/well). The absorbance was measured at 490 nm using the VERSAmax microplate reader.

Inhibitory rates were calculated according to the following formula:

Inhibitory rate (%)=(1−(OD value of compound−OD value of control well without enzyme)/(OD value of negative control well−OD value of control well without enzyme))×100.

The experimental results are shown in Table 2.

TABLE 2 c-MET inhibitory activity of compounds 1-28

| Compound | c-MET kinase inhibitory enzymatic activity $IC_{50}$ (nM) |
|---|---|
| 1 | 0.0022 |
| 2 | 0.0019 |
| 3 | 0.0016 |
| 4 | 0.0025 |
| 5 | 0.0021 |
| 6 | 0.0015 |
| 7 | 0.0022 |
| 8 | 0.0019 |
| 9 | 0.0017 |
| 10 | 0.0016 |
| 11 | 0.0025 |
| 12 | 0.0019 |
| 13 | 0.0017 |
| 14 | 0.0026 |
| 15 | 0.0013 |
| 16 | 0.0015 |
| 17 | 0.0016 |
| 18 | 0.0013 |
| 19 | 0.0019 |
| 20 | 0.0021 |
| 21 | 0.0014 |
| 22 | 0.0016 |
| 23 | 0.0015 |
| 24 | 0.0021 |
| 25 | 0.0023 |
| 26 | 0.0017 |
| 27 | 0.0019 |
| 28 | 0.0018 |
| Capmatinib | 0.0038 |

Referring to Table 2, the c-MET inhibitory activities of the compounds 1-28 were either greater than or at least equal to that of Capmatinib.

Example 12 the Anti-Proliferation Activities of Compounds

Experimental objective: To evaluate the anti-proliferation activities of the compounds against MKN-45 cells, EBC-1 cells, Hs746T cells and Vero cells.

Experimental methods: Tumor cell lines were cultured and periodically passaged, and cells in logarithmic growth phase were taken for plate spreading. The cells were stained with Trypan blue, counted and adjusted to an appropriate density. 50 μL of cell suspension was added into each well of a culture plate, and 50 μL of nutrient solution without cells was added into a blank control well. The culture plate was precultured for 24 h in an incubator under the condition of 37° C., 5% $CO_2$ and 100% relative humidity.

The DMSO stock solutions of the compounds 1-28 and Capmatinib were prepared, and diluted with Tecan D300e. Each compound was diluted to 7 concentration levels: 0.50 μM, 0.125 μM, 0.031 μM, 0.0078 μM, 0.0020 μM, 0.00049 μM, 0.00012 μM. The experiment was carried out in triplicate.

50 μL of the solution was added into each designated well, and the culture plate was incubated for 48 h. 50 μL of CTG working solution was added to each well. The culture plate was wrapped with aluminum foil to avoid light and shaken in the shaker for 2 min to induce cell lysis. The culture plate was placed at room temperature for 10 min to stabilize light-emitting signal which was detected with a 2014 EnVision plate reader. Experimental data was processed by GraphPad Prism 7 to calculate $IC_{50}$.

Experimental results are shown in Table 3.

TABLE 3

Anti-proliferation activities ($IC_{50}$) of the compounds 1-28.

| Compound | MKN-45 | EBC-1 $IC_{50}(\mu M)$ | Hs746T | Vero |
|---|---|---|---|---|
| 1 | 0.0015 | 0.0014 | 0.0016 | 0.129 |
| 2 | 0.0011 | 0.0012 | 0.0014 | 0.126 |
| 3 | 0.0015 | 0.0018 | 0.0015 | 0.101 |
| 4 | 0.0019 | 0.0018 | 0.0014 | 0.216 |
| 5 | 0.0016 | 0.0012 | 0.0016 | 0.138 |
| 6 | 0.0019 | 0.0019 | 0.0019 | 0.116 |
| 7 | 0.0013 | 0.0012 | 0.0018 | 0.127 |
| 8 | 0.0017 | 0.0018 | 0.0018 | 0.142 |
| 9 | 0.0018 | 0.0016 | 0.0014 | 0.252 |
| 10 | 0.0018 | 0.0019 | 0.0015 | 0.164 |
| 11 | 0.0014 | 0.0018 | 0.0014 | 0.231 |
| 12 | 0.0011 | 0.0017 | 0.0011 | 0.236 |
| 13 | 0.0012 | 0.0017 | 0.0014 | 0.152 |
| 14 | 0.0015 | 0.0012 | 0.0011 | 0.226 |
| 15 | 0.0016 | 0.0015 | 0.0013 | 0.238 |
| 16 | 0.0013 | 0.0013 | 0.0017 | 0.156 |
| 17 | 0.0012 | 0.0016 | 0.0012 | 0.123 |
| 18 | 0.0015 | 0.0011 | 0.0015 | 0.148 |
| 19 | 0.0019 | 0.0014 | 0.0014 | 0.251 |
| 20 | 0.0011 | 0.0018 | 0.0012 | 0.164 |
| 21 | 0.0012 | 0.0013 | 0.0011 | 0.132 |
| 22 | 0.0015 | 0.0017 | 0.0018 | 0.231 |
| 23 | 0.0017 | 0.0011 | 0.0014 | 0.157 |
| 24 | 0.0012 | 0.0012 | 0.0017 | 0.129 |
| 25 | 0.0013 | 0.0010 | 0.0013 | 0.192 |
| 26 | 0.0011 | 0.0018 | 0.0011 | 0.282 |
| 27 | 0.0013 | 0.0015 | 0.0018 | 0.163 |
| 28 | 0.0015 | 0.0012 | 0.0014 | 0.237 |
| Capmatinib | 0.0057 | 0.0039 | 0.0045 | 0.068 |

Referring to the experimental results, for the MKN-45 cell, EBC-1 cell and Hs746T cell, the compounds 1-28 showed more than twice the inhibitory activity of Capmatinib in vitro. For the Vero cell, $IC_{50}$ of Capmatinib is one-third to one-half that of the compounds 1-28, indicating that the toxicity of Capmatinib is higher than that of the compounds 1-28.

Example 13 In Vivo Anti-Tumor Assessment of Representative Compounds in Xenograft Tumor Model Experimental objective: To investigate in vivo efficacy of representative compounds on human lung squamous carcinoma cell (human EBC-1 cell) subcutaneous xenograft model.

Experimental methods: The EBC-1 cell xenograft tumor mouse model was used, according to the diameters of tumor, the tumor volume (TV), relative tumor volume (RTV), relative tumor proliferation rate (T/C (%)) and tumor growth inhibition value (TGI (%)) were calculated. Detailed dosing information is shown in Table 4.

TABLE 4

The Dosing Information

| Group | N | Compound | Dose (mg/kg) | Administration route | Frequency |
|---|---|---|---|---|---|
| 1 | 10 | Solvent | — | P.O. | QD × 15 days |
| 2 | 10 | Capmatinib | 10 | P.O. | QD × 15 days |
| 3 | 10 | Compound 1 | 10 | P.O. | QD × 15 days |
| 4 | 10 | Compound 16 | 10 | P.O. | QD × 15 days |
| 5 | 10 | Compound 17 | 10 | P.O. | QD × 15 days |

The changes in body weight of the mice are presented in FIG. 1.

Referring to FIG. 1, at the end of the experiment, the mice in group 2 (Capmatinib) experienced greater losses in body weight compared to those in the other groups, indicating that the toxicity of the Capmatinib may be higher than that of the compounds 1, 16 and 17.

TGI (%) or T/C (%) of the compounds was evaluated. TGI (%) reflects a tumor growth inhibitory rate. TGI (%) was calculated as follows: TGI (%)=[1−(average tumor volume at the end of administration in a treatment group−average tumor volume at the beginning of administration in the treatment group)/(average tumor volume at the end in a solvent control group−average tumor volume at the beginning in the solvent control group)]×100%.

T/C (%) was calculated as follows: T/C (%)=TRTV/CRTV×100%; where TRTV is treatment RTV, and CRTV is negative control RTV. According to the measurement results of the tumor, RTV was calculated, and the calculating formula for RTV is as follows: RTV=Vt/V0; where V0 is the average tumor volume measured on the day of first administration; and Vt is the average tumor volume measured on a specified day. TRTV and CRTV were measured on the same day.

The efficacy evaluation of tumor inhibition by Capmatinib, the compounds 1, 16 and 17 on human EBC-1 cell xenograft tumor model is shown in Table 5.

TABLE 5

Efficacy evaluation of tumor inhibition

| Group | Tumor Volume (mm³) (Day 15) | T/C(%) | TGI(%) |
|---|---|---|---|
| Solvent control | 901 ± 30 | — | — |
| Capmatinib | 225 ± 25 | 24.97 | 91.23 |
| Compound 1 | 136 ± 17 | 15.09 | 103.24 |
| Compound 16 | 162 ± 23 | 17.98 | 99.73 |
| Compound 17 | 184 ± 27 | 20.42 | 96.76 |

Figure 2:
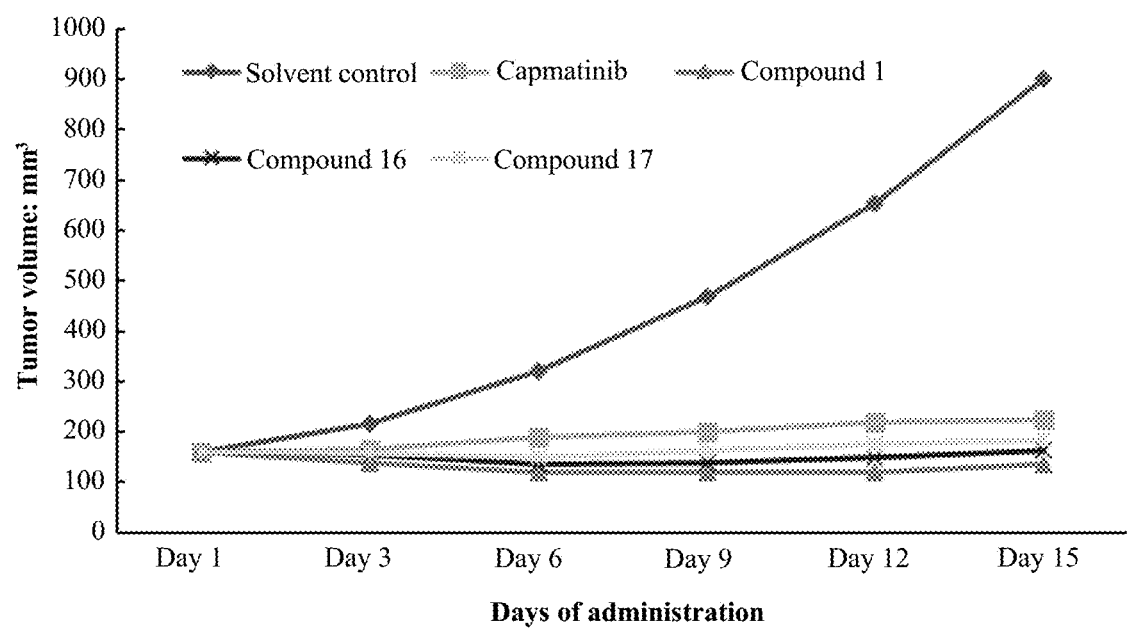
FIG. 2 shows tumor volume change curves of mice participating in the animal experiment according to example 13 of the present disclosure.

Tumor volume changes in the mice are shown in FIG. 2.

Referring to FIG. 2, at the end of the experiment, Capmatinib, as well as the compounds 1, 16 and 17 could effectively inhibit the growth of the tumor in mice. However, the compounds 1, 16 and 17 had better inhibitory effects.

Described above are only some embodiments of the present disclosure, which are described in a specific and detailed manner, and are not intended to limit the scope of this application. It should be noted that any modifications, variations and improvements made by those skilled in the art, without departing from the spirit of this application, shall fall within the scope of this application defined by the appended claims.

What is claimed is:
1. An imidazotriazine thiobenzamide derivative, or a pharmaceutically-acceptable salt thereof, wherein the imidazotriazine thiobenzamide derivative is selected from the group consisting of:
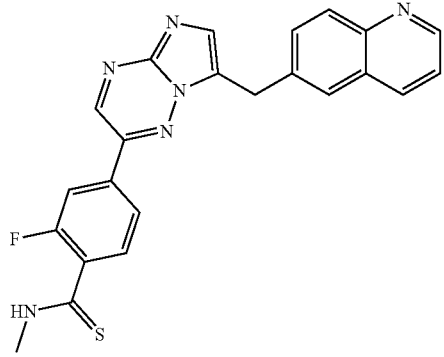
1
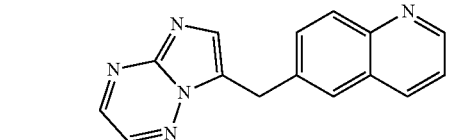
2
3
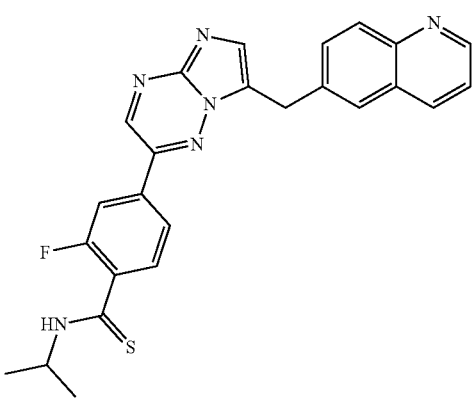 [SMILES: CC(C)NC(=S)c1ccc(-c2cnc3ncc(Cc4ccc5ncccc5c4)n3n2)cc1F]
-continued
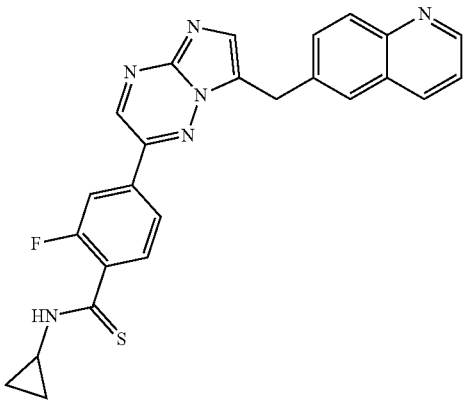 [SMILES: Fc1cc(-c2cnc3ncc(Cc4ccc5ncccc5c4)n3n2)ccc1C(=S)NC1CC1]
4
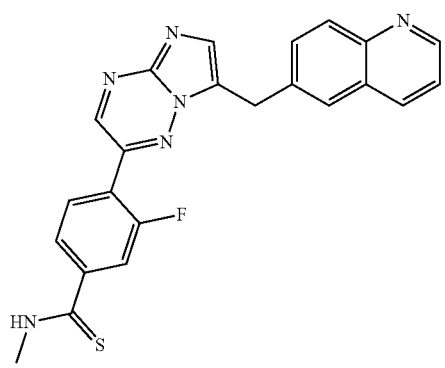
5
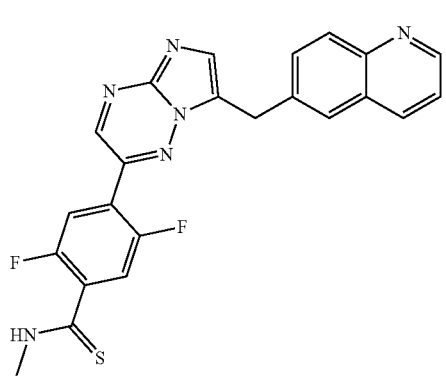
6
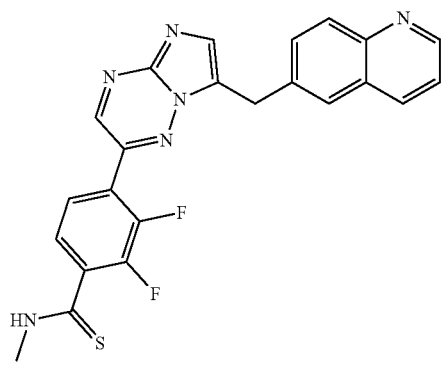
7

39
-continued
8
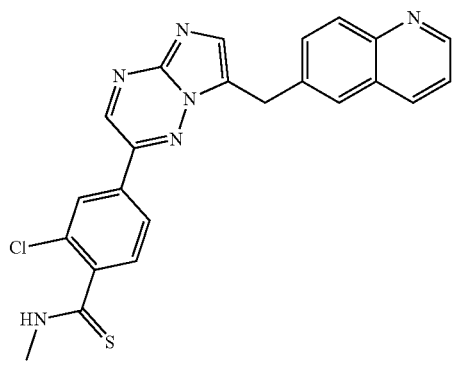 [SMILES: C=Cc1cc(Cc2cnc3ncc(-c4ccc(C(=S)NC)c(Cl)c4)nn23)ccc1N=C]
9
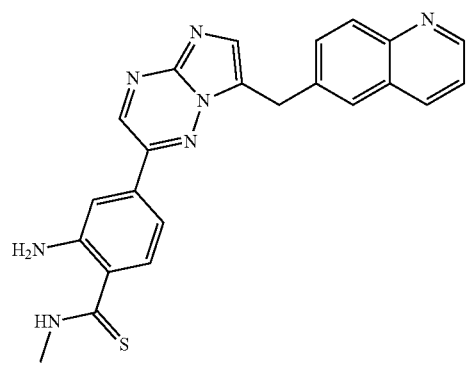 [SMILES: CNC(=S)c1ccc(-c2cnc3ncc(Cc4ccc5ncccc5c4)n3n2)cc1N]
10
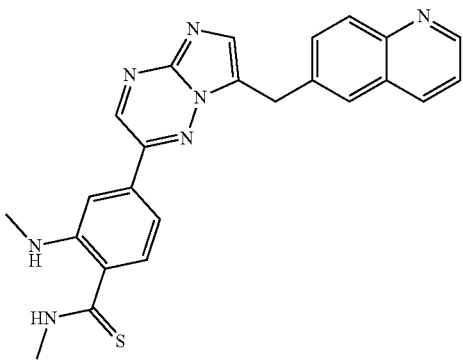 [SMILES: CNC(=S)c1ccc(-c2cnc3ncc(Cc4ccc5ncccc5c4)n3n2)cc1NC]
11
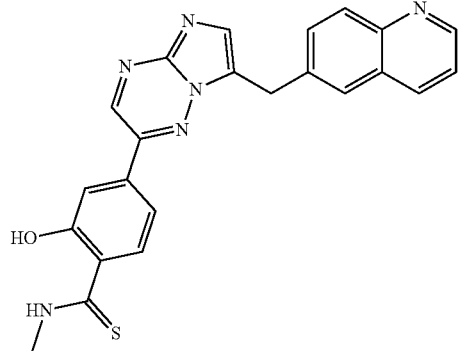 [SMILES: CNC(=S)c1ccc(-c2cnc3ncc(Cc4ccc5ncccc5c4)n3n2)cc1O]
40
-continued
12
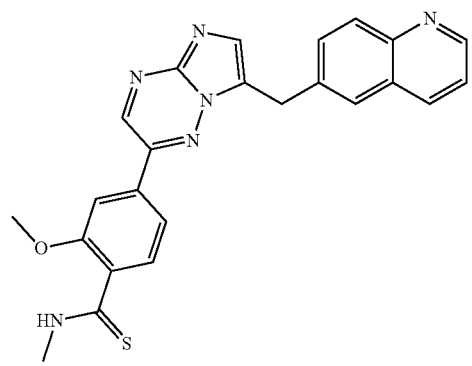
13
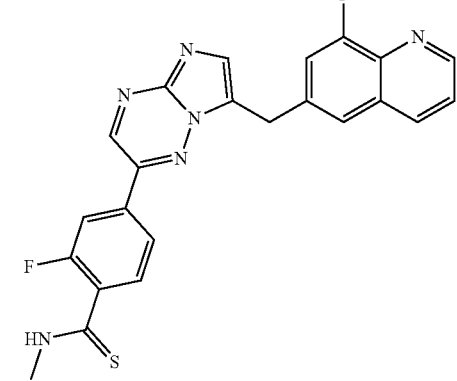
14
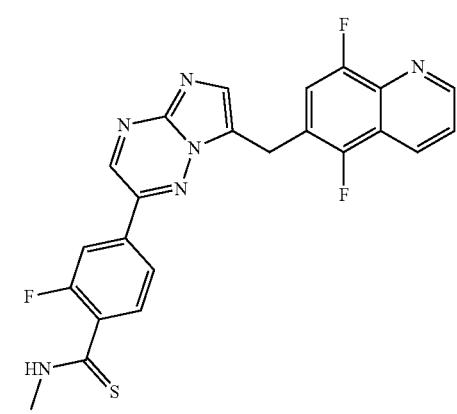 [SMILES: CNC(=S)c1ccc(-c2cnc3ncc(Cc4cc(F)c5ncccc5c4F)n3n2)cc1F]
15
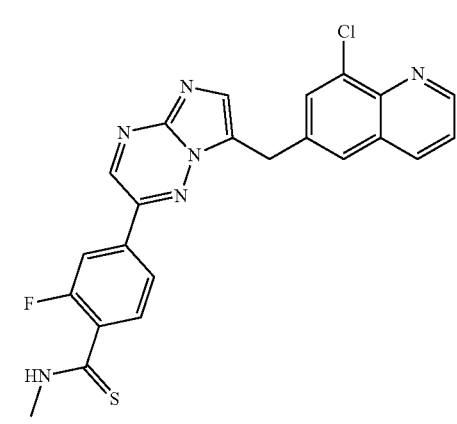 [SMILES: C=Cc1cc(Cc2cnc3ncc(-c4ccc(C(=S)NC)c(F)c4)nn23)cc(Cl)c1N=C]

-continued
16 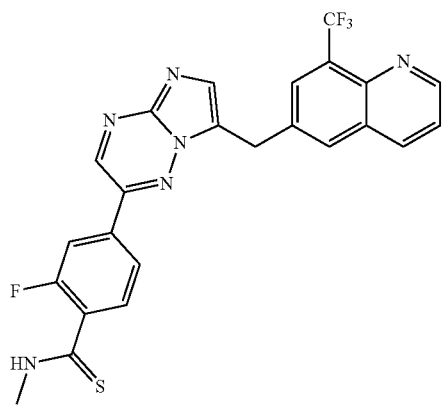 [SMILES: C=Cc1cc(Cc2cnc3ncc(-c4ccc(C(=S)NC)c(F)c4)nn23)cc(C(F)(F)F)c1N=C]
17 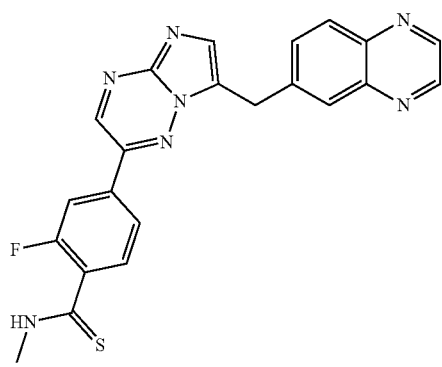 [SMILES: CNC(=S)c1ccc(-c2cnc3ncc(Cc4ccc5nccnc5c4)n3n2)cc1F]
18 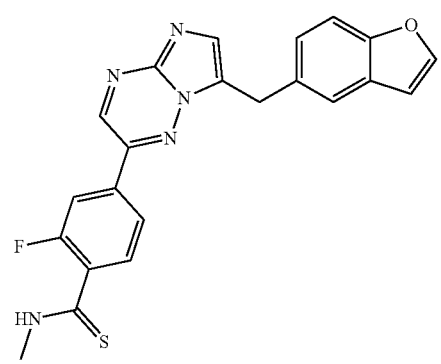 [SMILES: CNC(=S)c1ccc(-c2cnc3ncc(Cc4ccc5occc5c4)n3n2)cc1F]
19 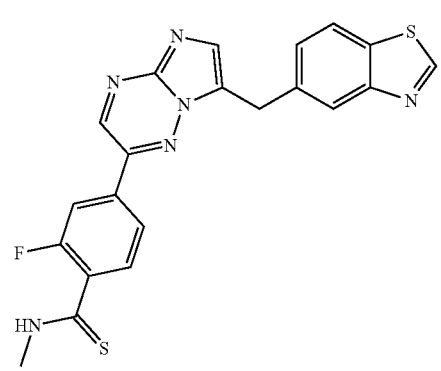
-continued
20 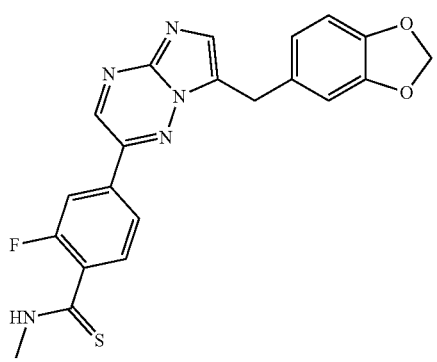 [SMILES: CNC(=S)c1ccc(-c2cnc3ncc(Cc4ccc5c(c4)OCO5)n3n2)cc1F]
21 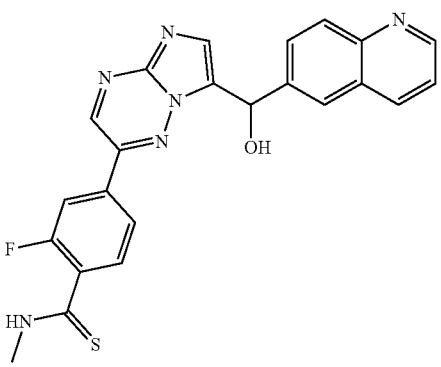
22 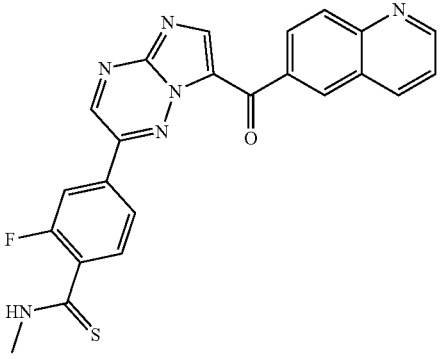
23 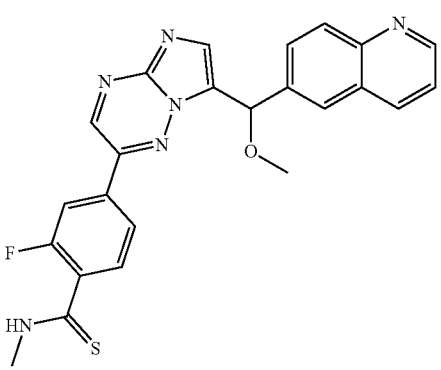

24

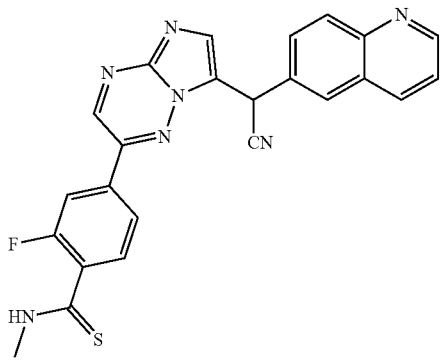

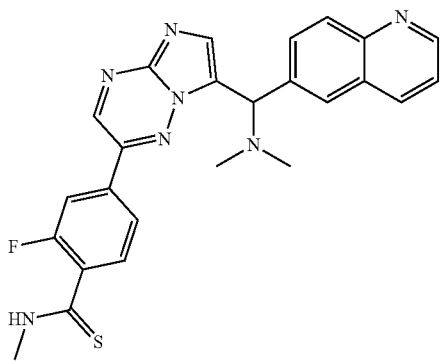

26

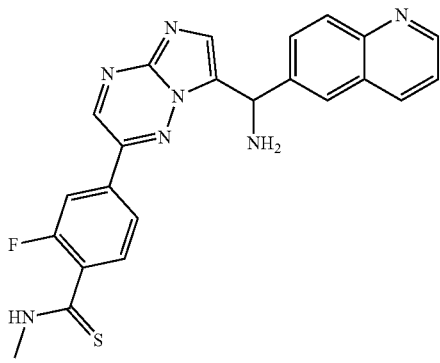

27

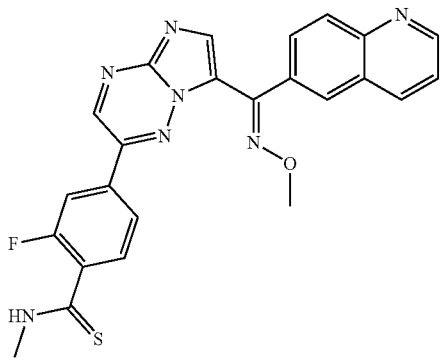

28

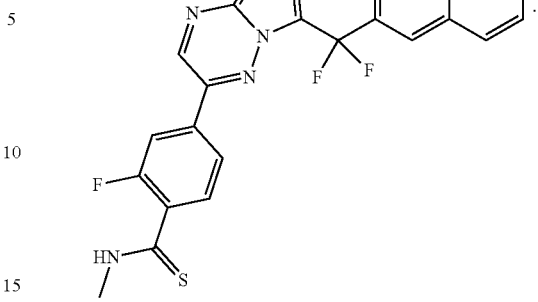

2. A drug or pharmaceutical composition, comprising:
   a therapeutically effective amount of the imidazotriazine thiobenzamide derivative of claim 1 or a pharmaceutically-acceptable salt thereof.

3. The drug or pharmaceutical composition of claim 2, further comprising:
   one or more of a pharmaceutically-acceptable carrier, a diluent and an excipient.

4. A method for treating a cancer in a subject in need thereof, comprising:
   administering a therapeutically effective amount of the imidazotriazine thiobenzamide derivative of claim 1 or a pharmaceutically-acceptable salt thereof to the subject;
   wherein the cancer is gastric cancer or lung cancer.

5. The method of claim 4, wherein the imidazotriazine thiobenzamide derivative or a pharmaceutically-acceptable salt thereof is administered in combination with an antitumor drug.

6. The method of claim 5, wherein the antitumor drug is selected from the group consisting of adriamycin, bleomycin, vinblastine, taxane, etoposide, 5-fluorouracil, cytoxan, methotrexate, cisplatin, tretinoin, temozolomide, actinomycin, imatinib, gefitinib, sorafenib, erlotinib, sunitinib, afatinib, cabozantinib, osimertinib, dabrafenib, rituximab, cetuximab, trastuzumab, nivolumab, pembrolizumab, atezolizumab, durvalumab, avelumab and a combination thereof.

7. A method for treating a cancer in a subject in need thereof, comprising:
   administering a therapeutically effective amount of the drug or pharmaceutical composition of claim 2 to the subject;
   wherein the cancer is gastric cancer or lung cancer.

8. The method of claim 7, wherein the drug or pharmaceutical composition is administered in combination with an antitumor drug.

9. The method of claim 8, wherein the antitumor drug is selected from the group consisting of adriamycin, bleomycin, vinblastine, taxane, etoposide, 5-fluorouracil, cytoxan, methotrexate, cisplatin, tretinoin, temozolomide, actinomycin, imatinib, gefitinib, sorafenib, erlotinib, sunitinib, afatinib, cabozantinib, osimertinib, dabrafenib, rituximab, cetuximab, trastuzumab, nivolumab, pembrolizumab, atezolizumab, durvalumab, avelumab and a combination thereof.

* * * * *